(12) United States Patent
McDunn et al.

(10) Patent No.: US 8,143,222 B2
(45) Date of Patent: Mar. 27, 2012

(54) MODULAR PLATFORM FOR TARGETED THERAPEUTIC DELIVERY

(75) Inventors: Jonathan E. McDunn, University City, MO (US); William G. Hawkins, Olivette, MO (US); Robert H. Mach, Eureka, MO (US); Richard A. Hotchkiss, Chesterfield, MO (US)

(73) Assignee: Washington University, Saint Louis, MO (US)

( * ) Notice: Subject to any disclaimer, the term of this patent is extended or adjusted under 35 U.S.C. 154(b) by 439 days.

(21) Appl. No.: 12/255,947

(22) Filed: Oct. 22, 2008

(65) Prior Publication Data

US 2009/0176705 A1   Jul. 9, 2009

Related U.S. Application Data

(60) Provisional application No. 60/981,747, filed on Oct. 22, 2007.

(51) Int. Cl.
*A61K 38/02* (2006.01)
*A61K 38/16* (2006.01)
*C07K 2/00* (2006.01)
*C07K 14/00* (2006.01)

(52) U.S. Cl. ............ 514/18.9; 514/19.3; 514/21.3; 514/21.4; 530/324; 530/326; 530/345; 530/402

(58) Field of Classification Search .................. None
See application file for complete search history.

(56) References Cited

U.S. PATENT DOCUMENTS

| | | | | |
|---|---|---|---|---|
| 6,093,382 | A * | 7/2000 | Wedeking et al. | 424/1.65 |
| 6,113,877 | A * | 9/2000 | Mach et al. | 424/1.65 |
| 6,713,280 | B1 * | 3/2004 | Huang et al. | 435/69.1 |
| 7,390,902 | B2 | 6/2008 | Mach et al. | |
| 2002/0061308 | A1 * | 5/2002 | Chang | 424/178.1 |
| 2003/0104985 | A1 * | 6/2003 | Matulic-Adamic et al. | 514/7 |
| 2004/0253307 | A1 * | 12/2004 | Hague et al. | 424/464 |
| 2005/0142181 | A1 * | 6/2005 | Li et al. | 424/450 |
| 2007/0161003 | A1 * | 7/2007 | Morris et al. | 435/6 |
| 2008/0107599 | A1 | 5/2008 | Mach et al. | |

OTHER PUBLICATIONS

Mach et al. Preparation of a technetium-99m SPECT agent for imaging the sigma-2 receptor status of solid tumors. Journal of Labelled Compounds and Radiopharmaceuticals. 2001, vol. 44, pp. 899-908.*

Choi et al, Development of a Tc-99 labeled sigma-2 receptor-specific ligand as a potential breast tumor imaging agent, Nucl Med Biol, 2001, 28:657-666.

(Continued)

*Primary Examiner* — Jeffrey E Russel
(74) *Attorney, Agent, or Firm* — Zackson Law LLC

(57) ABSTRACT

Pharmaceutical compounds, pharmaceutical compositions and methods of treatment are disclosed, wherein a compound comprises a targeting moiety which, in free form, binds a cell receptor with a dissociation constant $K_d$ of less than about $10^{-7}$ M, and a pharmaceutically active moiety, wherein the targeting moiety is other than an oligopeptide, a polypeptide, a peptidomimetic, a protein or a protein domain, and wherein the targeting moiety and the pharmaceutically active moiety are covalently attached. In some aspects, the targeting moiety binds a sigma-2 receptor with high affinity and high specificity, and the pharmaceutically active moiety is a pro-apoptotic peptide moiety. Methods of cancer treatment are disclosed comprising administering a disclosed pharmaceutical compound to a subject in need of thereof. The treatments selectively induce apoptosis in cancer cells. These methods can further comprise co-administration of radiation therapy and/or an additional chemotherapeutic agent.

10 Claims, 14 Drawing Sheets

OTHER PUBLICATIONS

Chu et al, Synthesis and in vitro binding of N-phenyl piperazine analogs as potential dopamine D3 receptor ligands, Bioorg Med Chem, 2005, 13:77-87.

Debatin and Krammer, Death receptors in chemotherapy and cancer, Oncogene, 2004, 23:2950-2966.

Efange et al, Vesamicol analogues as sigma ligands. Molecular determinants of selectivity at the vesamicol receptor, Biochem Pharmacol, 1995, 49:791-797.

Guelen et al, TAT-apoptin is efficiently delivered and induces apoptosis in cancer cells, Oncogene, 2004, 23:1153-1165.

Hashimoto and Ishiwata, Sigma receptor ligands: possible application as therapeutic drugs and as radiopharmaceuticals, Curr Pharm Des, 2006, 12:3875-3876.

Hiromura et al, Inhibition of Akt kinase activity by a peptide spanning the betaA strand of the proto-oncogene TCL1, J Biol Chem, 2004, 279:53407-53418.

Hotchkiss et al, TAT-BH4 and TAT-Bcl-xL peptides protect against sepsis-induced lymphocyte apoptosis in vivo, J Immunol, 2006, 176:5471-5477.

Hou et al, Characterization of a novel iodinated sigma-2 receptor ligand as a cell proliferation marker, Nucl Med Biol, 2006, 33:203-209.

Kashiwagi et al, Selective sigma-2 ligands preferentially bind to pancreatic adenocarcinomas: applications in diagnostic imaging and therapy, Mol Cancer, 2007, 6:48.

Kashiwagi et al, TAT-Bim induces extensive apoptosis in cancer cells, Ann Surg Oncol, 2007, 14:1763-1771.

Kassiou et al, Synthesis and in vivo evaluation of a new PET radioligand for studying sigma-2 receptors, Bioorg Med Chem, 2005, 13:3523-3626.

Kline et al, Novel antitumor prodrugs designed for activation by matrix metalloproteinases-2 and -9, Mol Pharm, 2004, 12:9-22.

Kung et al, Dopamine D-2 receptor imaging radiopharmaceuticals: synthesis, radiolabeling, and in vitro binding of (R)-(+)- and (S)-(−)-3-iodo-2-hydroxy-6-methoxy-N-[(1-ethyl-2-pyrrolidinyl)methyl]benzamide, J Med Chem, 1988, 31:1039-1043.

MacFarlane et al, Chronic lymphocytic leukemic cells exhibit apoptotic signaling via TRAIL-R1, Cell Death Differ, 2005, 12:773-782.

Mach et al, Ibogaine possesses a selective affinity for sigma 2 receptors, Life Sci, 1995, 57:PL57-62.

Maira et al, Carboxyl-terminal modulator protein (CTMP), a negative regulator of PKB/Akt and v-Akt at the plasma membrane, Science, 2001, 294:374-380.

Nader and Mach, Self-administration of the dopamine D3 agonist 7-OH-DPAT in rhesus monkeys is modified by prior cocaine exposure, Psychopharmacology (Berl.), 1996, 125:13-22.

O'Connor et al, Bim: a novel member of the Bcl-2 family that promotes apoptosis, EMBO J, 1998, 15:384-395.

Rowland et al, Synthesis and in vivo evaluation of 2 high-affinity 76Br-labeled sigma2-receptor ligands, J Nucl Med, 2006, 47:1041-1048.

Ryu et al, Intracellular delivery of p53 fused to the basic domain of HIV-1 Tat, Mol Cells, 2004, 17:353-359.

Schally and Nagy, Cancer chemotherapy based on targeting of cytotoxic peptide conjugates to their receptors on tumors, Eur J Endocrinol, 1999, 141:1-14.

Schwarze et al, In vivo protein transduction: delivery of a biologically active protein into the mouse, Science, 1999, 285:1569-1572.

Tan et al, Key roles of BIM-driven apoptosis in epithelial tumors and rational chemotherapy, 2005, 7:227-238.

Tu et al, Carbon-11 labeled sigma 2 receptor ligands for imaging breast cancer, 2005, 32:423-430.

Wheeler et al, Sigma-2 receptors as a biomarker of proliferation in solid tumors, Br J Cancer, 2000, 82:1223-1232.

* cited by examiner

SIGMA-2 LIGAND BINDING (A) HUMAN PANCREAS CANCERS (B) MURINE NORMAL AND TUMOR (C) Micro PET/CT of [$^{18}$F]4 Labeled Sigma-2 Ligand (WC26) in a Panc-02 Tumor Bearing Mouse.

SEQ ID NO: 2

SEQUENCE LISTING

```
<160> NUMBER OF SEQ ID NOS: 3

<210> SEQ ID NO 1
<211> LENGTH: 21
<212> TYPE: PRT
<213> ORGANISM: Homo sapiens

<400> SEQUENCE: 1

Glu Ile Trp Ile Ala Gln Glu Leu Arg Arg Ile Gly Asp Glu Phe Asn
1               5                   10                  15

Ala Tyr Tyr Ala Arg
            20

<210> SEQ ID NO 2
<211> LENGTH: 25
<212> TYPE: PRT
<213> ORGANISM: Homo sapiens
```

```
<400> SEQUENCE: 2

Leu Asp Pro Lys Leu Met Lys Glu Glu Gln Met Ser Gln Ala Gln Leu
1               5                   10                  15

Phe Thr Arg Ser Phe Asp Asp Gly Leu
                20                  25

<210> SEQ ID NO 3
<211> LENGTH: 21
<212> TYPE: PRT
<213> ORGANISM: Homo sapiens

<400> SEQUENCE: 3

Glu Ile Trp Ile Ala Gln Glu Ala Arg Arg Ile Gly Ala Glu Phe Asn
1               5                   10                  15

Ala Tyr Tyr Ala Arg
                20
```

MODULAR PLATFORM FOR TARGETED THERAPEUTIC DELIVERY

CROSS REFERENCE TO RELATED APPLICATION

This application claims benefit of priority to Provisional U.S. Patent Application No. 60/981,747 filed Oct. 22, 2007, which is incorporated herein by reference in its entirety.

REFERENCE TO GOVERNMENT SUPPORT

The invention was developed at least in part with the support of NIH grants GM055194 and GM044118. The government may have certain rights in the invention.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

BACKGROUND

In cancer chemotherapies, some chemotherapeutic agents are given systemically and exert their anti-cancer effects by exploiting differential metabolic or regulatory activity of cancer cells compared to non-cancer cells. The approach results in side effects including toxicity and immune suppression. Alternative approaches take advantage of differential receptor expression on cancer cells and use agonistic antibodies to initiate pro-death signaling pathways within cancer cells. However, transformed cells typically have defects in the response to pro-apoptotic stimuli. As a result of their general unresponsiveness to pro-apoptotic stimuli, many types of cancer cells are remarkably sensitive to slight perturbations in the balance between pro- and anti-apoptotic proteins. Furthermore, targeted therapies such as radiation and surgery are by their nature blind to distant metastases.

Many pharmaceuticals, such as chemotherapeutic agents, can be highly toxic to normal cells. Selective delivery of a pharmaceutical compound to a target cell population can therefore be advantageous (Schally and Nagy, European Journal of Endocrinology 141: 1-14, 1999). For example, cytotoxic peptide conjugates comprising both a peptide carrier which binds to a target receptor on tumor cells and a small molecule cytotoxic moiety such as doxorubicin, have been reported (Id.) Other strategies have been proposed or developed to target tumors. These strategies include physical targeting with radiation (Leibel, S. A., Semin. Oncol. 30: 596-615, 2003), physical targeting with intratumoral injection (Kashiwagi, H., et al., Ann. Surg. Oncol. 14: 1763-1771, 2007) targeting of receptors with antibodies (Kumar, P. S., et al., Semin. Oncol. 33: 386-391, 2006; Pangalis, G. A., et al., Curr. Topics Med. Chem. 6: 1657-1686, 2006), targeting receptors with ligands (MacFarlane, M., et al., Cell Death Differ. 12: 773-82, 2005), administering prodrugs that are activated by enzymes which are active in the local milieu (Kline, T., et al., Mol. Pharm. 1: 9-22, 2004) and exploiting differences in metabolic needs (Ippolito, J., et al., Proc Natl Acad Sci USA 103: 12505-12510, 2006; Nakajima, M., et al., Nippon Yakurigaku Zasshi 122: 482-490, 2003).

Programmed cell death or apoptosis is an essential process in cell homeostasis and eukaryotic development (Prochazkova, J. et al., Gen. Physiol. Biophys. 23: 209-229, 2004; Danial, N. N., et al., Cell 116: 205-219, 2004). Therefore, there is considerable interest in targeting the molecular pathways of apoptosis as a component of cancer therapy. Recent studies have shown that failure of apoptosis is both central to the evolution of cancer and related to resistance toward modern adjuvant treatment such as chemo- or radiation therapies (Debatin, K. M., et al., Oncogene 23: 2950-2966, 2004; Bergman, P. J., et al., Vet. Clin. North Amer. Small Animal Pract. 27: 47-57 1997; Tan, T. T., et al., Cancer Cell 7: 227-238, 2005). We and others have recently reported that intracellular delivery of pro-apoptotic peptides can induce apoptosis in cancer cells in vitro and in animal models of adenocarcinomas in vivo (Guelen, L., et al., Oncogene 23: 1153-1165, 2004; Ryu, J., et al., Mol. Cells. 17: 353-359, 2004; Kashiwagi, H., et al., Ann. Surg. Oncol. 14: 1763-1771, 2007; Schwarze, S. R., Science 285: 1569-1572, 1999). For example, TAT-Bim is a dual domain peptide molecule comprised of an internalization peptide motif (the polybasic region of HIV-1 TAT) and a biological effector peptide domain (the apoptosis-inducing BH3 domain of Bim). Antitumor effectiveness of such compounds in vivo could be demonstrated by injecting them intra-tumorally due to the non-specific cell permeation capacity of the TAT peptide (Schwarze, S. R., Science 285: 1569-1572, 1999). Direct intra-tumoral injection of the TAT-Bim compound effectively reduced tumor size and prolonged survival in animal models of pancreatic cancer (Kashiwagi, H., Ann. Surg. Oncol. 14: 1763-1771, 2007).

Each of these various approaches has inherent limitations; for example, physical targeting has no ability to treat distant metastases, and antibody-based targeting approaches can be hampered by barriers to accessibility of a macromolecular carrier. Accordingly, new approaches are needed.

SUMMARY

In view of a need for new pharmaceuticals and methods which selectively target cell populations such as cancer cells, the present inventors have developed pharmaceutical compounds, as well as pharmaceutically acceptable salts, prodrugs or hydrates thereof, as well as methods of treatment that utilize these molecules. A compound of the present teachings, or a pharmaceutically acceptable salt, prodrug or hydrate thereof, comprises at least two domains, including a) a targeting moiety which, in free form, binds a cell receptor with a dissociation constant $K_d$ of less than about $10^{-7}$ M; and b) a pharmaceutically active moiety, wherein the targeting moiety is other than an oligopeptide, a polypeptide, a peptidomimetic, a protein or a protein domain, and wherein the targeting moiety and the pharmaceutically active moiety are covalently attached. In some configurations, a compound, pharmaceutically acceptable salt, prodrug or hydrate thereof of the present teachings can induce apoptosis selectively in cells of a targeted cell population, such as a cancer cell population, without inducing apoptosis in non-targeted cells.

The present inventors have also developed pharmaceutical compositions comprising such compounds, pharmaceutically acceptable salts, prodrugs or hydrates thereof, and at least one pharmaceutically acceptable excipient and/or carrier. In some aspects, a pharmaceutical composition can also include one or more additional pharmaceutically active compounds, such as a chemotherapeutic agent. In some configurations, a chemotherapeutic agent can be an established chemotherapeutic such as gemcitabine.

The present teachings also include methods of cancer treatment. In various aspects, these methods include administering to a subject an effective amount of a pharmaceutical composition comprising a compound, a pharmaceutically acceptable salt, a prodrug or a hydrate thereof, wherein the compound comprises a targeting moiety which binds a sigma-2 receptor with a dissociation constant $K_d$ less than the dissociation constant $K_d$ between the targeting moiety and a sigma-1 receptor, and further comprises a pharmaceutically active moiety which as apoptosis-inducing activity, such as, without limitation, a proapoptotic peptide. In various configurations of these methods, a pharmaceutical composition can further comprise a carrier, an excipient, and/or an additional pharmaceutical agent such as a chemotherapeutic agent. In yet other configurations, a method can comprise administering a composition comprising a compound of the present teachings, and administering a composition comprising a chemotherapeutic agent. The administering can comprise administering a compound of the present teachings and a chemotherapeutic agent, in a combined formulation or separate formulations. In some configurations, a chemotherapeutic agent can be gemcitabine. In yet other configurations, a method of cancer treatment can include administering to a subject an effective amount of a pharmaceutical composition of the present teachings, along with radiation therapy. In various configurations of these methods, the effects of co-administration of a compound of the present teachings and an additional chemotherapeutic agent and/or radiation therapy can be additive or supra-additive. In various aspects, a subject can be a mammal, such as a human patient in need of treatment, a companion animal such as a cat or dog, or an agricultural animal such as a cow, sheep, pig or goat.

Cancer treatment methods of the present teachings also include methods comprising selecting a pharmaceutical composition on the basis of the composition comprising a pharmaceutical compound comprising a non-peptide targeting moiety which selectively targets a proapoptotic moiety to a sigma-2 receptor of tumor cells, and administering an effective amount of the composition to a subject in need of treatment for a cancer. In some configurations, the subject can have cancerous cells such as pancreas adenocarcinoma cells; upon administration to such subjects, the compound selectively targets a proapoptotic moiety to the cancer cells or cancer cell organelles, such as mitochondria, lysosomes, or the endoplasmic reticulum comprised by the cancer cells. In some configurations, the compound can selectively deliver a proapoptotic moiety such as a proapoptotic peptide to mitochondria comprised by cancer cells. Hence, in various aspects, a cancer treatment method can comprise administering a compound of the present teachings comprising a sigma-2 receptor ligand moiety and a proapoptotic peptide moiety.

In yet other teachings, the present inventors disclose use of a therapeutic agent described herein for the manufacture of a medicament for treatment of a disease such as a cancer.

In additional aspects, methods are provided for inducing apoptosis in a cell. These methods comprise contacting the cell with a compound of the present teachings. The methods can further comprise inducing apoptosis selectively within a cell or cells comprised by a target cell population without inducing apoptosis in non-targeted cells. In various configurations, a target cell population can be cancerous cells, and non-targeted cells can be non-cancerous cells, such as cancerous cells and non-cancerous cells comprised by a mammalian subjects such as a human in need of treatment for a cancer.

In various aspects of the present teachings, a compound or a pharmaceutically acceptable salt, prodrug or hydrate thereof can comprise a non-peptide targeting moiety which, in free form, binds a cell receptor with a dissociation constant $K_d$ of less than about $10^{-7}$ M, less than about $10^{-8}$ M, or less than about $10^{-9}$ M. In addition, in various aspects, a targeting moiety can have a molecular mass of less than about 1200 Da, less than about 1000 Da, less than about 800 Da, or less than about 400 Da. In some aspects, a targeting moiety can be conjugated to a fluorescent or radioactive labeling moiety. In various configurations, such a labeling moiety can include any fluorophore or radioisotope known to skilled artisans, and can have a molecular weight of 500 Daltons or more, without the targeting moiety losing appreciable affinity or specificity. In various configurations, the targeting moiety can bind a sigma receptor, such as a sigma-2 receptor, and in some configurations, the targeting moiety can bind a sigma-2 receptor with a dissociation constant $K_d$ less than the dissociation constant $K_d$ between the targeting moiety and a sigma-1 receptor.

In various aspects, a targeting moiety which binds a sigma-2 receptor can comprise any moiety which, in free form, has activity as a sigma-2 receptor ligand, and binds a sigma-2 receptor with high affinity (i.e., a $K_d$ less than about $10^{-7}$ M). In some configurations, a targeting moiety can comprise a N-substituted 9-azabicyclo[3.3.1]nonan-3α-yl phenylcarbamate, such as a structure described in U.S. patent application Ser. No. 11/776,533 of Mach et al., or can be a N-substituted 9-azabicyclo[3.3.1]nonan-3α-yl phenylcarbamate of structure

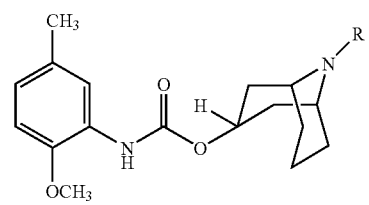

wherein R can be a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, a $C_1$-$C_{10}$ arylamino, an ester and a hydrophilic polymer such as a polyethylene glycol. In some configurations, when R is a bond, the bond can be a single, double or triple bond with a carbon atom, and/or a heteroatom such as a nitrogen, an oxygen or a sulphur. In some aspects, an N-substituted 9-azabicyclo[3.3.1]nonan-3α-yl phenylcarbamate can have the structure

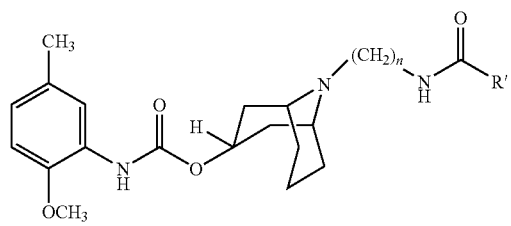

wherein n is an integer from 1 to about 10, and R' can be a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, a $C_1$-$C_{10}$ arylamino, an ester and a hydrophilic polymer such as a polyethylene glycol. In some configurations, when R is a bond, the bond can be a single, double or triple bond with a carbon atom, and/or a heteroatom such as a nitrogen, an oxygen or a sulphur. In some aspects, n can be 6. In various embodiments, either R or R' can represent a covalent bond extending between the targeting moiety and a pharmaceutically active moiety.

In various other configurations, a sigma-2 receptor ligand can have a structure comprising a 5,6-dialkoxytetrahydroisoquinoline, such as a benzamide compound comprising a 5,6-dimethoxytetrahydroisoquinoline described in U.S. patent application Ser. No. 10/903,771 of Mach et al., or U.S. patent application Ser. No. 11/757,246 of Mach et al., which are hereby incorporated by reference.

In addition, in various configurations, a targeting moiety can have a structure which includes a ligand for a dopamine receptor, such as, without limitation, a $D_2$ receptor ligand or a $D_3$ receptor ligand. Accordingly, a targeting ligand of a compound of the present teachings can be a $D_2$ receptor ligand such as an S-(−) isomer of 3-iodo-2-hydroxy-6-methoxy-N-[(1-ethyl-2-pyrrolidinyl)methyl]benzamide (IBZM) (Kung, H. F., et al., J. Med. Chem. 31: 103901043, 1988) or a $D_3$ receptor ligand such as an N-phenyl piperazine analog (Chu, W. et al., Bioorg Med. Chem. 13: 77-87, 2005), or 7-hydroxy-N,N-di-n-propyl-2-aminotetralin (7-OH-DPAT) (Nader, M. A., and Mach, R. H., Psychopharmacology (Berl.) 125: 13-22, 1996).

In various configurations, the targeting moiety of a compound of the present teachings can be a small molecule moiety (i.e., having a molecular weight between about 50 Da and about 1200 Da), such as, without limitation, colchicine, taxol, cytochalasin, latrunculin, chlorpromazine, spidamine, reserpine, phorbol, a phorbol ester such as 12-O-tetradecanoylphorbol-13-acetate, pioglitazone (Actos™), MK-886 (Rouzer, C. A., et al., J. Biol. Chem. 265: 1436-1442, 1990), somatostatin receptor agonist, 506BD (Somers, P. K., et al., J. Am. Chem. Soc. 113: 8045-8056, 1991), methallylrapamycin, rapamycin, or an isatin Michael acceptor (U.S. Patent application 60/840,747, R. H. Mach et al., inventors).

In various aspects, a pharmaceutically active moiety of a compound of the present teachings can be a peptide moiety, an oligonucleotide moiety or a bioactive small molecule moiety, i.e., a moiety having a molecular weight of between about 50 Da and about 1200 Da. can be of a compound of the present teachings. In various configurations, a pharmaceutically active moiety of a compound of the present teachings can be a small molecule moiety such as, without limitation, gemcitabine, rapamycin, paclitaxel, or 5-fluorouracil.

In various aspects, a pharmaceutically active moiety of a compound, salt, prodrug or hydrate thereof can be a cytotoxic moiety, such as an apoptosis-inducing peptide. Hence, an apoptosis-inducing peptide can comprise a proapoptotic polypeptide such as a Bim polypeptide (O'Connor, L., et al., EMBO J. 17: 384-395, 1998), a variant thereof having apoptosis-inducing activity, a carboxyl terminal modulator protein (CTMP) (Maira, S. M., et al., Science 294, 374-380, 2001) or a variant thereof having apoptosis-inducing activity. In various aspects, such a variant can have at least 50% sequence identity, at least 60% sequence identity, at least 70% sequence identity, at least 75% sequence identity, at least 80% sequence identity, at least 85% sequence identity, at least 90% sequence identity, or at least 95% sequence identity with a proapoptotic polypeptide such as Bim or CTMP.

In some aspects, an apoptosis-inducing peptide or variant thereof can be an apoptosis-inducing domain, portion or motif of a proapoptotic polypeptide such as a BH3 domain of Bim, a variant thereof which has apoptosis-inducing activity, an apoptosis-inducing domain, portion or motif of CTMP which has apoptosis-inducing activity, or a variant thereof having apoptosis-inducing activity. In some configurations, a BH3 domain of Bim can comprise, consist of, or consist essentially of the amino acid sequence EIWIAQELRRIG-DEFNAYYAR (SEQ ID NO: 1). In some configurations, an apoptosis-inducing domain of CTMP can comprise, consist of, or consist essentially of the amino acid sequence LDP-KLMKEEQMSQAQLFTRSFDDGL (SEQ ID NO: 2). In some aspects, a pharmaceutically active moiety can comprise a variant of these sequences if it has at least 50% sequence identity, at least 60% sequence identity, at least 70% sequence identity, at least 75% sequence identity, at least 80% sequence identity, at least 85% sequence identity, at least 90% sequence identity, or at least 95% sequence identity with either SEQ ID NO: 1 or SEQ ID NO: 2, provided the variant has apoptosis inducing activity.

In some aspects, a pharmaceutically active moiety of a compound can be a biologically active nucleic acid, such as an siRNA.

Hence, in various aspects, a pharmaceutical compound, or pharmaceutically acceptable salt, prodrug or hydrate thereof, can include a targeting moiety comprising a structure

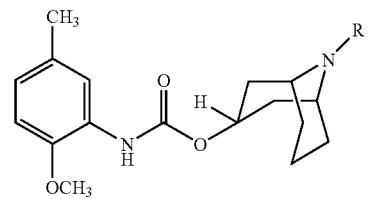

wherein R is as defined herein, and can be covalently attached to a pharmaceutically active peptide moiety of sequence EIWIAQELRRIGDEFNAYYAR (SEQ ID NO: 1) or LDP-KLMKEEQMSQAQLFTRSFDDGL (SEQ ID NO: 2), or a variant thereof which has at least 50% sequence identity with either SEQ ID NO: 1 or SEQ ID NO: 2 and retains apoptosis-inducing activity. In various configurations, the percentage of sequence identity with a peptide of SEQ ID NO: 1 or SEQ ID NO: 2 can be at least 60%, at least 70%, at least 70%, at least 80%, at least 85%, at least 90%, or at least 95%, provided the variant has apoptosis inducing activity. Similarly, in various configurations of these aspects, the targeting moiety can comprise a structure

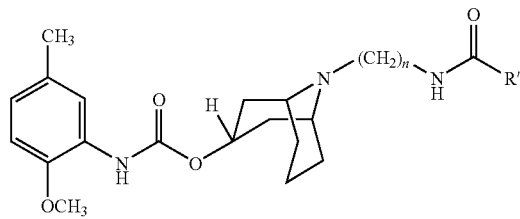

wherein R' is as defined herein, and n is an integer from 1 to about 10. In some configurations, n can be 6.

In various aspects, the present inventors have established, inter alia, that a dual domain sigma-2 ligand-BH3 construct (S2-BH3) induces apoptosis in cancer cells such as pancreas cancer cells in vitro, and a short course of S2-BH3, such as in a murine model of cancer, can prolong survival with minimal toxicity. In various aspects, a therapy of the present teachings which comprises administration of a compound disclosed herein can be combined with anti-metabolite and/or radiation therapies.

BRIEF DESCRIPTION OF THE DRAWINGS

FIG. 1A illustrates human pancreatic cancer lines that demonstrate sigma-2 ligand binding. FIG. 1B illustrates FACS histograms that demonstrate high fluorescence in tumor cells with low levels in normal tissues in tumor bearing mice receiving an intraperitoneal dose of fluorescent sigma-2 ligand WC26. FIG. 1C illustrates Micro PET/CT images of pancreas adenocarcinoma (Panc-02) bearing C57BL/6 mice administered $^{18}$F-labled sigma-2 ligand).

DETAILED DESCRIPTION

Figure 1:
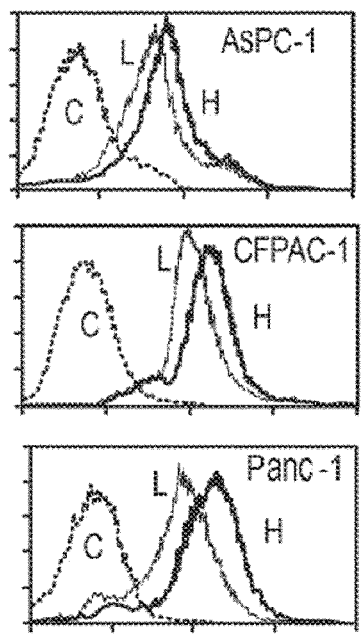
FIG. 1 illustrates that sigma-2 receptors are expressed in a limited fashion in normal tissues but are highly expressed in murine pancreatic cancer and human and murine pancreatic cancer cell lines.
Figure 1:
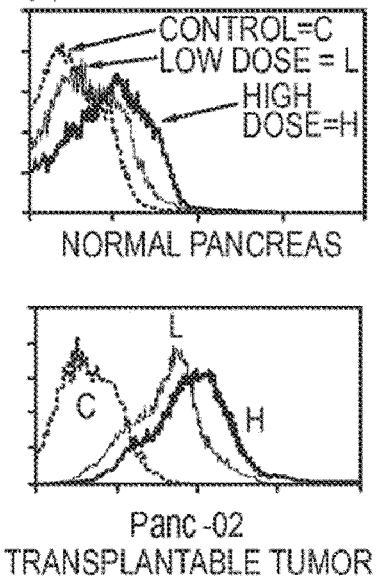
Figure 1:
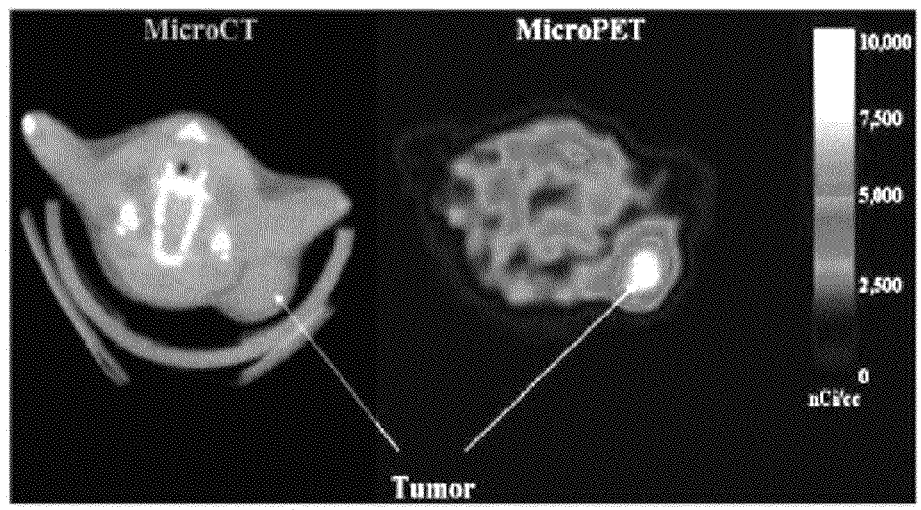

The present inventors have developed a new molecular approach to chemotherapy. In their discoveries, they have developed pharmaceutical compounds comprising a) a targeting moiety which, in free form, binds a cell receptor with a dissociation constant $K_d$ of less than about $10^{-7}$ M; and b) a pharmaceutically active moiety, wherein the targeting moiety is other than an oligopeptide, a polypeptide, a peptidomimetic, a protein or a protein domain, and wherein the targeting moiety and the pharmaceutically active moiety are covalently attached. In some configurations, a compound, pharmaceutically acceptable salt, prodrug or hydrate thereof of the present teachings can include a proapoptotic moiety as a pharmaceutically active moiety. Such a compound, when contacted with cells, can induce apoptosis selectively in cells of a targeted cell population, such as a tumor cell population, without inducing apoptosis in non-targeted cells.

In various embodiments, a cell receptor of the present teachings can be any cell structure which has a small molecule ligand (i.e., a ligand of molecular weight of less than about 1200 Da, less than about 1000 Da, less than about 800 Da, or less than about 400 Da). The cell structure can be, without limitation, a receptor protein or polypeptide such as a cell surface protein, a transmembrane protein or a cytosolic protein. The receptor can be localized in the cell to an organelle such as a mitochondrion, or can be within the cytosol. The dissociation constant $K_d$ between a free form of a targeting moiety of the present teachings and its receptor can be, in various aspects, $10^{-7}$ M or less, $10^{-8}$ M or less, or $10^{-9}$ M or less. Without limitation, a receptor of the present teachings can be a receptor whose expression is limited to a subset of cell types, such as a sigma-2 receptor, which is overexpressed in several types of cancers but has limited expression in normal tissues (Waterhouse, R. N. et al., Nucl. Med. Biol. 24:127-134, 1997; Crawford, K. W. et al., Cancer Res. 62: 313-322, 2002; Kassiou, M., et al., Bioorg. Med. Chem. 13: 3623-3626, 2005; Wheeler, K. T., et al., Br. J. Cancer 82: 1223-1232, 2000; Hashimoto, K. et al., Curr. Pharm. Des. 12: 3857-3876, 2006). A targeting moiety of the present teachings can bind the sigma-2 receptor with high specificity. For example, a dissociation constant $K_d$ between the targeting moiety and a sigma-2 receptor can be less than that between the targeting moiety and a sigma-1 receptor. In some configurations, a targeting moiety can be a "small molecule" ligand, i.e., a non-peptidyl moiety having a molecular weight of less than about 1200 Da, and can, for example, comprise an N-substituted 9-azabicyclo[3.3.1]nonan-3α-yl phenylcarbamate, such as a structure

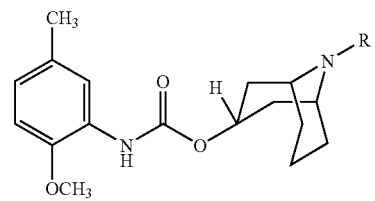

wherein R is selected from the group consisting of a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, an ester and a hydrophilic polymer.

Molecules of the present teachings further comprise a pharmaceutically active moiety such as, for example, a proapoptotic peptide. Some non-limiting examples of proapoptotic peptides are the BH3 region of Bim (O'Connor, L., et al., EMBO J. 17: 384-395, 1998) or an apoptosis-inducing region of a polypeptide which targets an Akt kinase, such as CTMP (Maira, S. M., et al., Science 294: 374-380, 2001; Hiromura, M., et al., J. Biol. Chem. 279: 53407-53418, 2004; Chae, K-S., et al., J. Neurophys. 93: 1174-1182, 2005). A molecule of the present teachings comprising a targeting moiety and a proapoptotic peptide moiety can selectively deliver an apoptosis-inducing amount of the proapoptotic peptide moiety to cancer cells. The present inventors have found that such molecules have increased toxicity to cancer cells, and can be expected to have fewer side effects, compared to other anticancer compounds. The present inventors also envision that effective amounts of these molecules will be less than nontargeted chemotherapeutics, and will be agnostic as to whether they are acting on a tumor mass or a metastatic site. In addition, administration of these compounds can be effective in vivo with virtually no systemic effects. For example, blood chemistry panel and immune cell counts are preserved.

EXAMPLES

The following examples provide non-limiting illustrations of the present teachings. While some of examples may include conclusions about the way the invention may function, the inventor do not intend to be bound by those conclusions, but put them forth only as possible explanations. Unless noted by use of past tense, presentation of an example does not imply that an experiment or procedure was, or was not, conducted, or that results were, or were not actually obtained.

The methods and compositions described herein utilize or are produced using laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999, and Ausubel, F. M., et al., ed., Current Protocols in Molecular Biology. For pharmaceutical compositions and methods of treatment disclosed herein, dosage forms and administration regimes can be determined using standard methods known to skilled artisans, for example as set forth in standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. Organic syntheses including synthesis of radiolabelled organic compounds can be performed using methods and principles well known to skilled artisans, such as those set forth in standard texts such as Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

In addition, some experiments presented in the Examples below may use some of the following materials and methods.

In some experiments presented herein, pancreatic cancer cell lines such as AsPC-1, BxPC-3, CFPAC-1, Panc-1, and Panc-02 (American Type Culture Collection, Manassas, Va.) are maintained in supplemented RPMI medium containing glutamine (2 mml/L), pyruvate (1 mmol/L), penicillin and streptomycin (100 IU/ml), and 10% fetal calf serum.

Tumor Challenge and Serial Tumor Measurements

In culture Panc-02 cells are grown for 3 passages and 50,000 cells are given intradermally over the right hind limb of a mouse using a TB syringe. The intradermal location is used to facilitate accurate tumor measurements. Tumor diameter is measured with calipers every two days in two dimensions and the data are recorded. Mice are euthanized when the tumors reach 2 cm or ulcerate. In the subcutaneous model, 100,000 Panc-02 cells are utilized.

Peptides

Peptides are commercially synthesized using HOBt/Fmoc chemistry, purified by reverse phase HPLC to >95% purity and the amino acid composition confirmed by amino acid analysis and MALDI-TOF mass spectrometry. Peptides are dissolved in DMSO at 20 mg/ml and stored at −70° C. until use. Peptides used include: S2-BH3, S2-BH3-inactive, S2-CTMP, S2-CTMP-inactive, TAT-BIM, TAT-BIM (inactive), TAT-CTMP, and TAT-CTMP (inactive).

Sigma-2 Receptor Ligands

Sigma-2 receptor ligands of the present teachings are synthesized by published methods (Choi, S. R., et al., Nucl. Med. Biol. 28:657-666, 2001; Efange, S. M., et al., Biochem. Pharmacol. 49: 791-797, 1995; Hou, C., et al., Nucl. Med. Biol. 33: 203-209, 2006; Rowland, D. J., et al., J. Nucl. Med. 47:1041-1048, 2006; Mach, R. H., et al., Synapse 58: 267-274, 2005; Mach, R. H., et al., Life Sci. 57: L57-L62, 1995).

Apoptosis Determination

Tumor Cells are seeded at a density of 0.2 to 0.5×106 cells per mL in 12-well plates and incubated at 37° C. for at least 24 hours (murine cancer cells) or 48 hours (Human cancer cells). After incubation, S2-fusion protein is added to the cell culture medium. The cells are then incubated for 18 hours (active caspase 3) or 24 hours (TUNEL) at 37° C. in humidified 5% $CO_2$. Apoptosis is detected by FACS analysis after staining cells for active caspase-3 (Cell Signaling, Boston, Mass.) or with the APO-BRDU kit (Phenix Flow Systems, San Diego, Calif.). Briefly, cells are washed with PBS, treated with trypsin-EDTA to remove adhesion molecules, and washed again. After centrifugation at 1,200 rpm for 10 min, cells are fixed with 1% paraformaldehyde and washed with PBS. After centrifugation at 1,800 rpm for 10 min, cells are fixed with 90% methanol at −20° C. and washed with PBS. Each pellet is resuspended in 1:100 anti-active caspase-3 antibody (1 µg/ml caspase 3, PBS with 5% FBS) or Br-duTP with TdT, and incubated overnight at 4° C. After washing, each pellet is resuspended in 1:100 FITC labeled secondary antibody, dUTP-specific fluorescein-PRB1 antibody (Phoenix Flow System, Inc., San Diego, Calif.) or 500 µl 7AAD buffer (Calbiochem, San Diego, Calif.) and incubated for 1 hour at room temperature. Cell fluorescence signals is determined using a FACScan flow cytometer (BD Biosciences) and analyzed with CellQuest software (BD Biosciences) to measure the percentage of apoptotic cells.

Example 1

This example illustrates sigma-2 receptor expression in vitro and in vivo.

In this example, flow cytometry and sigma-2 ligands labeled with the fluorophore fluorescein isothiocyanate or the radioisotope $^{18}F$ were used to demonstrate that sigma-2 receptors are expressed in a limited fashion in normal murine tissues such as kidney, liver, lung, heart, brain, lymph node, spleen and pancreas, but are highly expressed in murine pancreatic cancer (Kashiwagi, H., et al., Mol. Cancer. 6: 48, 2007). In these experiments, as illustrated in FIG. 1, human pancreas cancer cell lines CFPAC-1, Panc-1, and AsPC-1 (available from American Type Culture Collection, Manassas, Va. and grown according to the supplier's instructions) were incubated for 5 minutes with a fluorescent sigma-2 receptor ligand (L=low dose, 50 nM), (H=high dose, 100 nM) or were left unstained (Control). (A) All human pancreas cancers showed dose dependent labeling with ligand. (B)

Tumor bearing mice received an intraperitoneal dose of fluorescent sigma-2 ligand WC26,

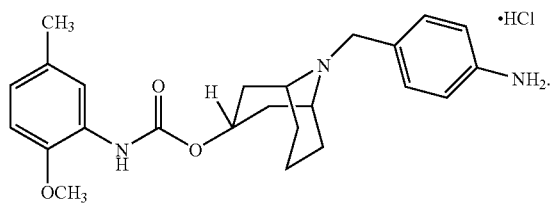

Mice were euthanized and single cell suspensions were made from pancreas, liver, spleen lung, kidney, brain and tumor. FACS histograms of fluorescent intensity from normal murine pancreas cells and syngeneic pancreatic tumor (Panc-02). FACS histograms demonstrate high fluorescence in tumor cells with low levels in normal tissues. In addition, the $K_d$ and $B_{max}$ values of receptor-radioligand binding were 4.88 nM and 1250 fmol/mg protein, respectively. (C) Micro PET/CT of a murine Panc-02 pancreas adenocarcinoma-bearing C57BL/6 mouse which had been given systemic $^{18}$F-labeled Sigma-2 ligand. The tumor is indicated by arrows and was approximately 1 cm$^3$. The tumor lights up intensely on PET compared to normal tissues. The additional hot spot represents metastatic tumor in a regional lymph node. Other studies have shown the distribution of sigma-2 receptors in normal human tissues and that it mirrors the distribution of sigma-2 receptors in the mouse (Kashiwagi, H., et al., Ann. Sur. Oncol. 14: 1763-1771, 2007; Tu, Z., et al., Nucl. Med. Biol. 32: 423-430, 2005). Hence, in conjunction with previous studies, in vivo administration of an $^{18}$F-labeled sigma-2 ligand and microPET imaging reveals that sigma-2 receptors are preferentially found in the murine pancreas tumor as compared to normal tissues.

Example 2

This example illustrates intracellular distribution of sigma-2 ligands and their potential as therapeutic delivery vehicles.

Figure 2:
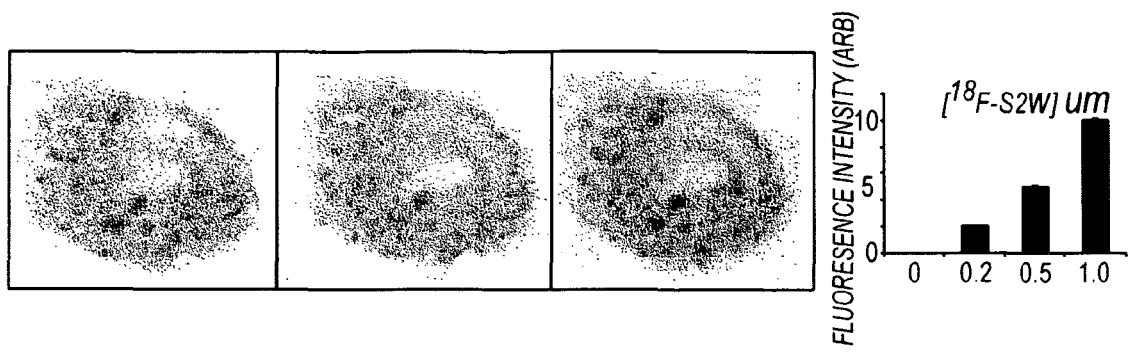
FIG. 2 illustrates that sigma-2 ligands are rapidly internalized and colocalize with mitochondria.

In this example, as shown in FIG. 2, two-photon microscopy of a single cell (Zeng, C., et al., Cancer Res. 67: 6708-6716, 2007) indicates intracellular distribution of: left panel, fluorescently-labeled sigma-2 ligand (10 µM); second panel, mitochondria (MitoTracker (Invitrogen Corporation, Carlsbad, Calif.), 50 nM); third panel, the merged image. Brightest (yellow in original) pixels show colocalization of the fluorescent sigma-2 ligand with mitochondria. The right panel shows the dose-dependent uptake of fluorescently labeled sigma-2 ligand. These data show that ligands to the sigma-2 receptor are rapidly internalized in a dose dependent fashion and are subsequently distributed throughout the cell, partially co-localizing with lysosomal, mitochondrial and endoplasmic reticulum markers. Moreover, these sigma-2 ligands have been conjugated to fluorescent and radiotracer compounds with molecular weights of at least 500 Daltons without losing appreciable affinity or specificity. These data indicate that sigma-2 ligands can be used not only for tumor imaging but also as vehicles to deliver therapeutic molecules to various intracellular compartments in sigma-2 receptor-bearing cells.

Example 3

Figure 3:
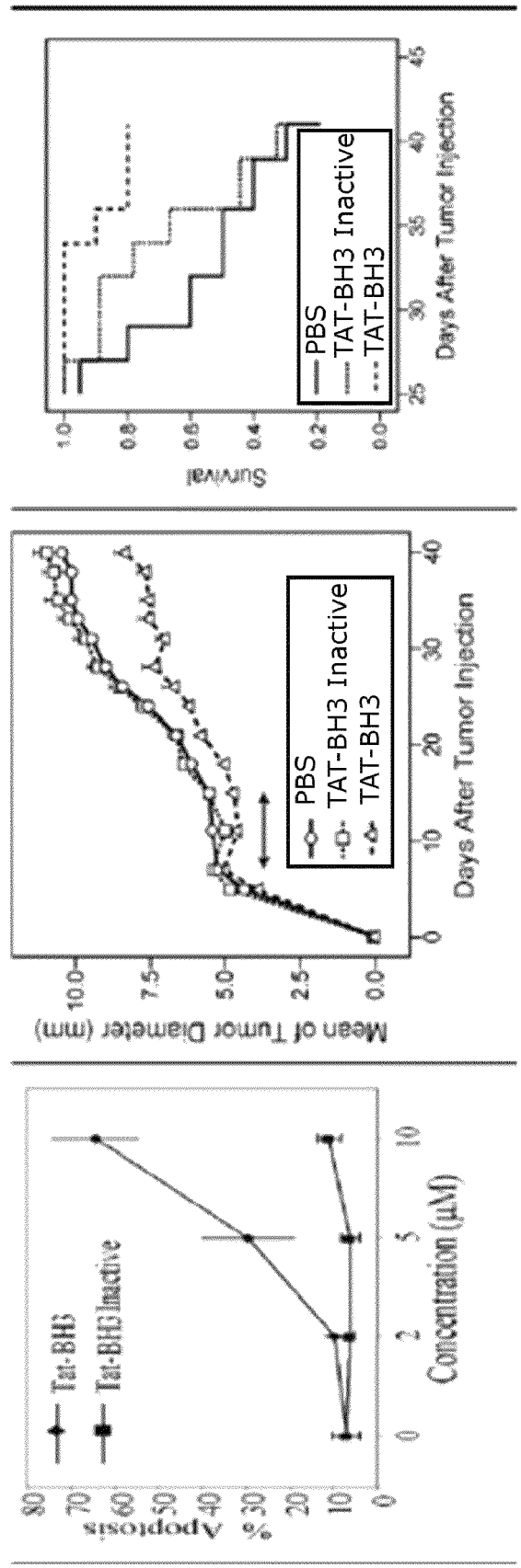
FIG. 3 illustrates that TAT-BH3 induces pancreas cancer cell death in vitro and in vivo.

This example illustrates BH3-induced apoptosis in pancreas cancer, wherein delivery of proteins/peptides into cells was accomplished using the protein transduction domain of the TAT protein from the human immunodeficiency virus (HIV)-1 as a carrier (Hotchkiss, R. S., et al., J. Immunol. 176: 5471-5477, 2006; Tanaka, Y., et al., J. Immunol. 170:1291-1298, 2003; Schwarze, S. R., et al., Trends Cell Biol. 10: 290-295, 2000; Schwarze, S. R., et al., Science 285:1569-1572, 1999). In these experiments, the Tat protein transduction domain was synthetically combined with the Bim-BH3 domain to generate TAT-BH3. In addition, a control peptide was synthesized with two amino acid substitutions in the Bim-BH3 domain rendering an inactive domain, TAT-BH3-inactive (Kashiwagi, H., et al., Ann. Surg. Oncol. 14: 1763-1771, 2007). These constructs permit proof-of-principle experiments to demonstrate that intracellular delivery of BH3 or CTMP4 induces apoptosis. As shown in FIG. 3, TAT-BH3 induces pancreas cancer cell death in vitro and in vivo. Id. These data show that intracellular delivery of BH3 through TAT leads to activation of caspase-3 and apoptosis in pancreas cancer cells.

Utilizing a FITC labeled antibody specific for Bim we demonstrate that our TAT-BH3 construct was able to gain access to the intra-cellular compartment in a dose dependent fashion. Id. Furthermore, as shown in FIG. 3, FACS analysis for caspase-3 activation and analysis by TUNEL assay demonstrate that TAT-Bim induces apoptosis in a dose dependent fashion while inactivated TAT-BH3 (TAT-BH3 Inactive) has no effect (FIG. 3, left panel).

In these experiments, we tested the combination of TAT-BH3 with and without radiation and demonstrated augmentation of the number of pancreas cancer cells undergoing apoptotic cell death as measured by active caspase-3. (Kashiwagi, H., et al., Ann. Surg. Oncol. 14: 1763-1771, 2007). In these experiments, intratumoral injection of 200 µg TAT-BH3 for 7 consecutive days inhibited pancreas cancer growth and prolonged survival of tumor bearing mice (FIG. 3, middle and right panels). Id. In contrast, administration of TAT-BH3 inactive did not significantly alter tumor growth or survival compared to mice treated with PBS only. Treatment of the murine cancer cell line Panc-02 with TAT-BH3 for 6 days induced apoptosis in a dose dependent fashion in vitro (left panel, p<0.0001). Intratumoral injection of TAT-BH3 (indicated by arrow in graph) significantly retards tumor growth in vivo (FIG. 3, middle panel, p<0.0001). We conclude that intratumoral injection of TAT-BH3 into a Panc-02 tumor provides a significant survival advantage (FIG. 3, right panel, p<0.02).

Example 4

This example illustrates CTMP-induced apoptosis of pancreas cancer cells.

Figure 4:
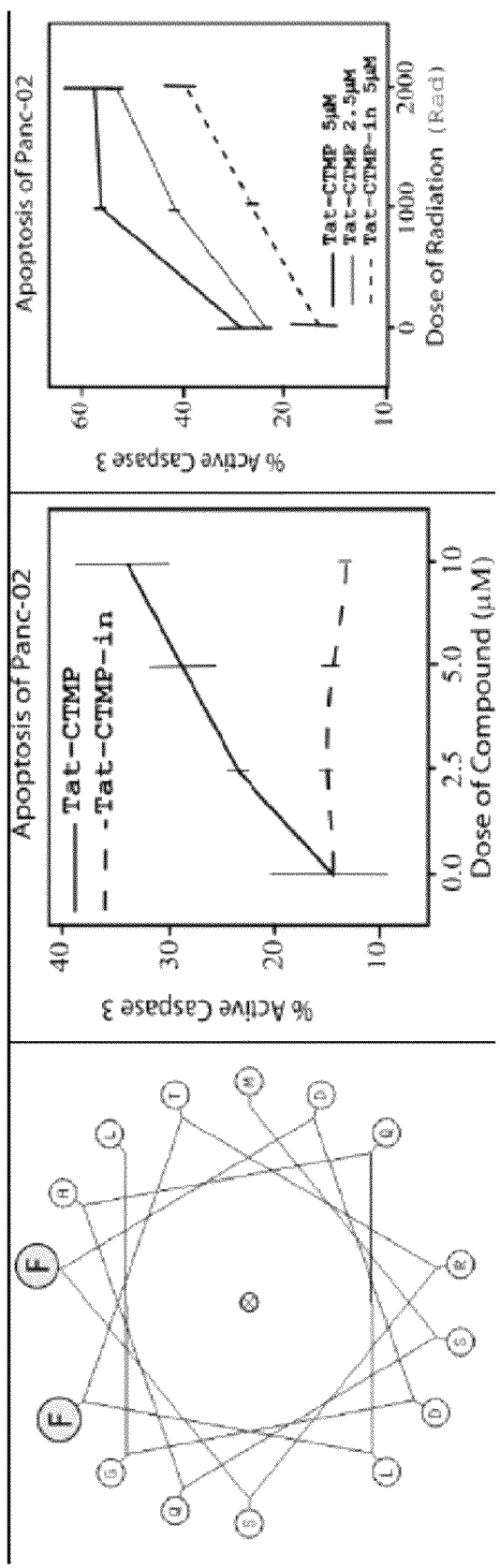
FIG. 4 illustrates that intracellular delivery of CTMP leads to apoptosis.

CTMP binds to the C-terminal regulatory domain of Akt, inhibiting phosphorylation of Ser$^{473}$ and activation of Akt, and thereby promotes apoptosis. CTMP is highly conserved between mouse and human (85% of the residues are identical or conservative replacements) and has two functional domains, a highly structured N-terminal domain and a C-terminal thioesterase domain. Within the N-terminal domain there are four peptides that have structural elements that meet the criteria described by Maira et al (Science 294: 374-380, 2001) as mediating the interaction with Akt. In these experiments, we synthesized TAT-fusion peptides of each of these four domains and screened them for their ability to induce apoptosis in pancreas cancer cells. As shown in FIG. 4, one of the peptides, CTMP4, induced appreciable apoptosis in both human and murine pancreas cancer cells while a rationally-designed mutant lacking two bulky residues on one face of the helix (Tat-CTMP-in) had no appreciable activity. In FIG. 4, the left panel (A), presents a helical wheel diagram (Schiffer, M. and Edmundson, A. B., Biophys. J. 7, 121-135, 1967) of the active domain of CTMP. The shaded residues are mutated to alanine in the inactive control peptide (Tat-CTMP-in). In the middle panel (B), representative data demonstrate the dose-dependency of pancreas cancer cell apoptosis induced by TAT-CTMP. In the right panel (C), representative data demonstrate that TAT-CTMP sensitizes pancreas cancer cells to radiation-induced apoptosis in a dose dependent fashion. Furthermore, cotreatment with TAT-CTMP4 and radiation results in increased apoptosis (FIG. 4, right panel). These data demonstrate that inhibition of Akt through binding of small synthetic peptides to the regulatory domain of Akt leads to induction of apoptosis.

Example 5

This example illustrates that a combination of gemcitabine and results in an additive increase in apoptosis, and that TAT-CTMP-mediated induction of apoptosis occurs via inhibition of the Akt pathway.

In these experiments, a combination of gemcitabine, a commonly-used chemotherapeutic drug for pancreas cancer and Tat-CTMP were tested in our in vitro model. In this study, two human pancreas adenocarcinoma cell lines (Panc-1 and AsPC-1) were treated with TAT-CTMP and TAT-CTMP in in the presence and absence of gemcitabine (30 nM). The combination of TAT-CTMP with gemcitabine (FIG. 5A, solid line) results in an additive increase in apoptosis. The data shown for TAT-CTMP-inactive parallels the response observed with gemcitabine alone.

In order to demonstrate that the TAT-CTMP-mediated induction of apoptosis was occurring via inhibition of the Akt pathway, Western blot analyses were performed on cell lysates in the presence of TAT-CTMP and controls (FIGS. 5B and 5C). Human pancreas adenocarcinoma, Panc-1, was grown in culture and treated with TAT-CTMP, TAT CTMP-Inactive, wortmannin (PI3-kinase inhibitor), DMSO (vehicle control for wortmannin), and PBS, and immunoblots were probed with anti-total Akt and anti-phospho Akt (Ser-473). In addition we looked at down stream effector GSK-3β using antibodies directed at GSK-3β and phospho GSK-3β. The data suggest that our positive control (wortmannin) as well as TAT-CTMP result in decreased active phospho-AKT one hour after treatment, providing mechanistic support for the cell signaling processes involved in the TAT-CTMP-mediated induction of apoptosis.

Figure 5:
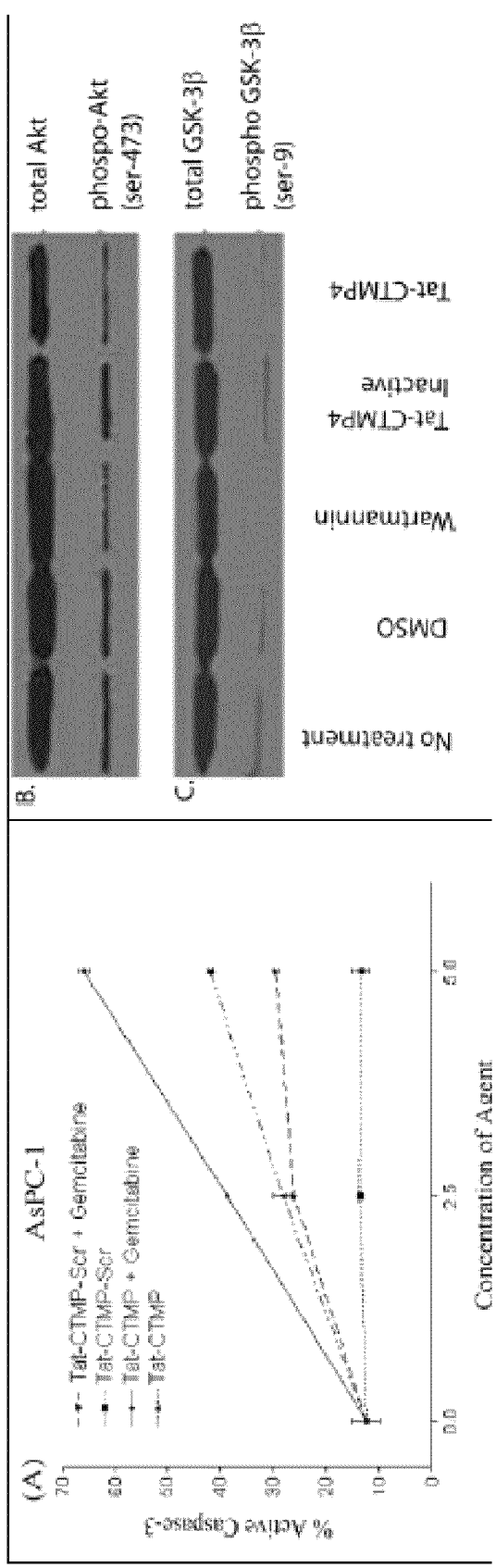
FIG. 5 illustrates that (A) combination therapy utilizing Tat-CTMP in the presence of gemcitabine results an in additive response with respect to the induction of apoptosis; (B and C) antitumor effects of CTMP4 are the result of inhibition of Akt3 and its downstream effectors.

As illustrated in FIG. 5, (A) combination therapy utilizing Tat-CTMP in the presence of gemcitabine results an in additive response with respect to the induction of apoptosis. In these experiments, the human pancreas adenocarcinoma cell line AsPC-1 was treated with Tat-CTMP-Scramble (Tat-CTMP-Scramble=Tat-CTMP-Inactive) and Tat-CTMP at 0 μM (PBS-only), 2.5 μM, and 5 μM concentrations in the presence and absence of gemcitabine for 24 hours. Cells were subsequently harvested and % active caspase-3 was assessed by flow cytometry. Each experimental group represents an n=3. Results are expressed as the mean, with bars representing standard error of the mean. This experiment was repeated twice with multiple murine and human lines with similar results. (B and C) Antitumor effects of CTMP4 are the result of inhibition of Akt3 and its downstream effectors. (B) Model human pancreatic adenocarcinoma (Panc-1) was treated with PBS (no treatment control), DMSO (vehicle control for wortmannin), wortmannin (an inhibitor of phosphatidylinositol 3-kinase (PI-3), mitogen-activated protein kinase (MAPK) and myosin light-chain kinase (MLCK), Mizutani, T., et al., Angew. Chem. Int. Ed. 41: 4680-4682, 2002) (1 μM), TAT-CTMP Inactive (10 μM), and TAT-CTMP (10 μM). Samples were treated for 1 hour prior to preparation of cell lysates. Immunoblots were subsequently prepared and stained with (B) anti-total AKT and phospho-AKT (Ser$^{473}$) and (C) anti-total GSK-3β and phospho GSK-3β.

Example 6

This example illustrate preparation of the Sigma-2-BH3 peptide.

Figure 6:
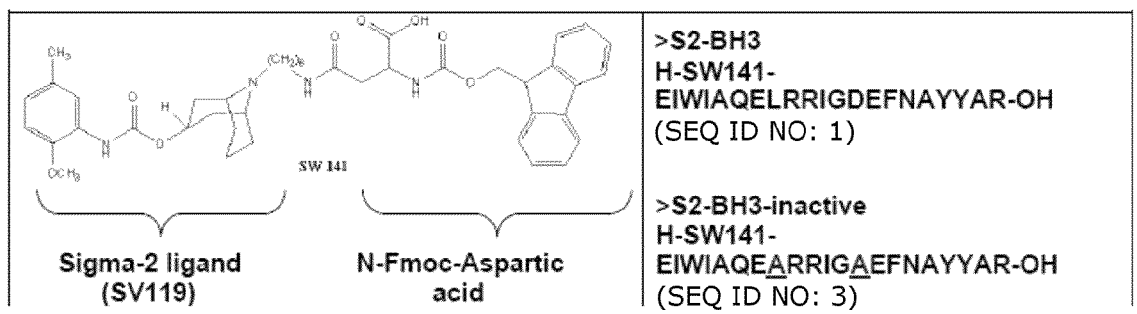
FIG. 6 illustrates compound SW141, a precursor molecule comprising a Sigma-2 ligand which serves as a targeting moiety in peptides of the present teachings (left panel), as well as active and inactive Sigma-2 ligand-BH3 peptides (right panel).

In this example, 5 grams of a novel aspartic acid derivative, SW141 (FIG. 6, left panel) comprising the sigma-2 ligand SV119,

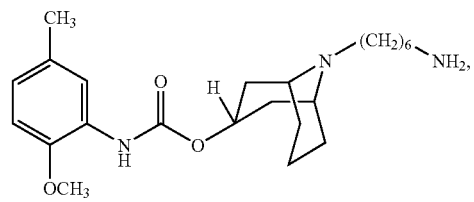

as its side chain, was synthesized. In these experiments, compound SW141 was incorporated in solid phase peptide synthesis (SPPS) of the BH3 domain used in TAT-Bim-BH3 constructs using standard Fmoc/HOBT chemistry. Two peptides were synthesized for these studies, sigma-2 ligand-Bim-BH3 (S2-BH3) and S2-BH3-inactive (FIG. 6, right panel). S2-BH3-inactive is incapable of binding to and inhibiting the anti-apoptotic Bcl-2 family members (for example, Bcl-2 and Bcl-x(L)). The BH3 and BH3-inactive domains were synthesized using automated SPPS. Prior to side chain deprotection and cleavage from the resin, 5-fold molar excess SW141 was added to each sequence manually. Approximately 60 milligrams of each peptide (~95% purity) was obtained for our initial studies. In FIG. 6, the left panel shows that SW141 is comprised of the sigma-2 receptor-specific ligand, SV119 covalently bound to aspartic acid through a flexible alkyl linker. The right panel shows the FASTA-formatted sequences of S2-BH3, comprising amino acid sequence EIWIAQELRRIGDEFNAYYAR (SEQ ID NO: 1) and control peptide SW-BH3-inactive comprising amino acid sequence EIWIAQEARRIGAEFNAYYAR (SEQ ID NO: 3), used in preliminary studies. SW141 refers to the novel sigma-2 amino acid (left panel) and the underscored residues are mutations resulting in an inactive peptide.

Example 7

This example illustrates that S2-BH3, comprising a sigma-2 receptor-binding targeting moiety and a BH3 proapoptotic peptide moiety, induces apoptosis at significantly higher levels in pancreas cancer cells than either SV119 or TAT-BH3 alone.

Figure 7:
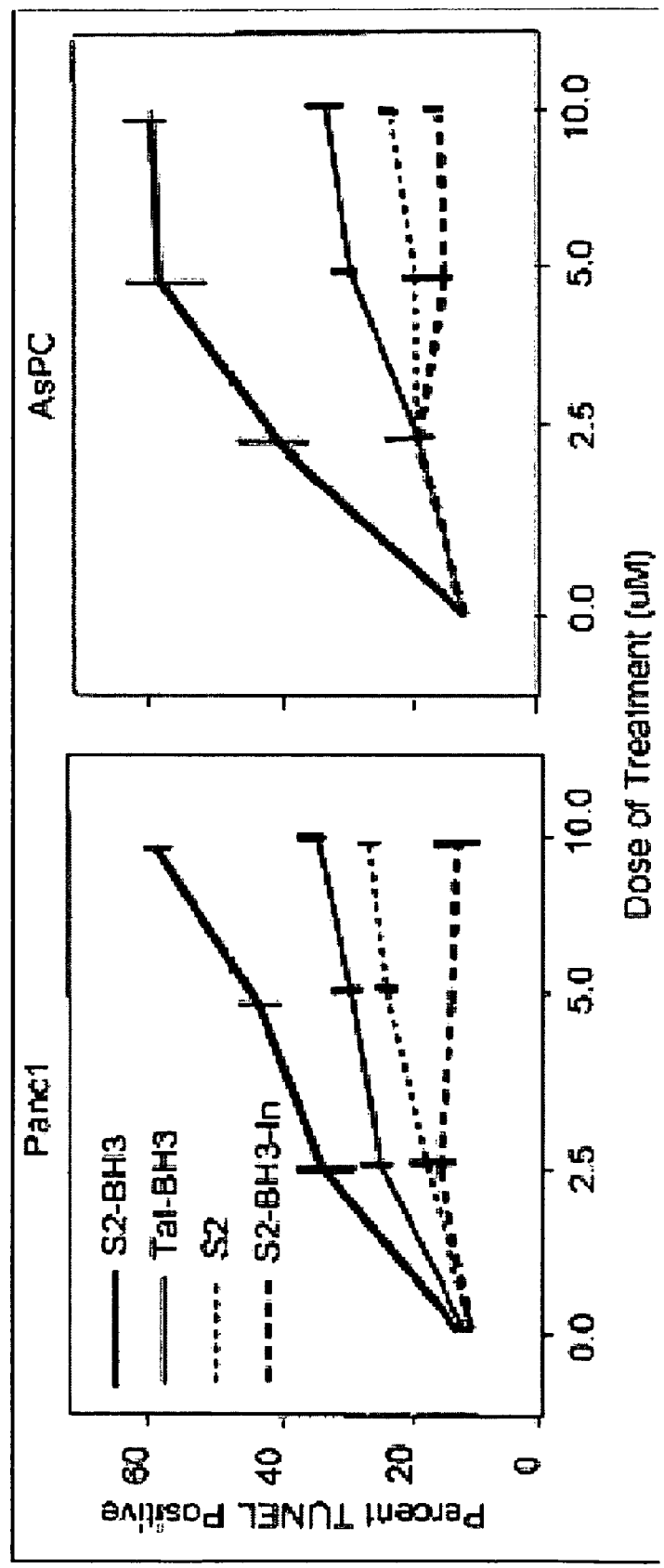
FIG. 7 illustrates that treatment with S2-BH3 leads to significant apoptosis.

In these experiments, the toxicity of the novel fusion compound, S2-BH3, was studied in both murine and human pancreatic cancer cell lines. FIG. 7 presents representative data demonstrating the apoptotic response of both human and murine pancreatic cancer cells to the prototypic sigma-2 ligand-targeted peptide, S2-BH3. As shown in FIG. 7, a dose-dependent apoptotic response to S2-BH3 was observed in pancreas cancer cell lines from both species. In contrast, the mutated, inactive S2-BH3-in peptide caused no appreciable apoptosis even at a dose of 10 μM. Treatment with the sigma-2 ligand S2 (which is the side chain of the N-terminal residue of the S2-BH3 peptide) induced a low, concentration-dependent level of apoptosis in both human and murine pancreas cancer cell lines, as did treatment with TAT-BH3. Cells were treated with one of four compounds (S2-BH3, S2-BH3-in, S2 (SV119 is the targeting domain of S2-BH3) or TAT-BH3 (the effector domain of S2-BH3. Error bars represent SEM. The level of S2-BH3-induced apoptosis was comparable to that of a combination of S2 alone and TAT-BH3, suggesting an additive effect.

Example 8

This example illustrates that systemic delivery of S2-BH3 slows tumor growth and prolongs survival in vivo.

In these experiments, we have completed the first in vivo administration of our novel therapeutic. Using large (14 day) established murine pancreas cancers (7-8 mm in mean diameter, flank) in C57BL/6 mice, we administered seven systemic doses (intraperitoneal injection) over 14 days. Treatment with 400 μg of S2-BH3 but not vehicle control (DMSO) or inactivated S2-BH3 (S2-Bh3-in) resulted in reduction in tumor growth rate and prolonged survival (Table 1, p<0.0001). No systemic toxicity was noted in any of the treatment animals when assessed by biochemical analysis (liver function tests, creatinine, amylase, and blood counts), systemic behavior or by immunohistochemistry of organs (liver, pancreas, lung, heart, brain and spleen). We conclude that treating of a subject with cancer with a pharmaceutical compound of the present teachings can significantly improve survival in the subject.

TABLE 1

S2-BH3 prolongs survival in vivo

| Treatment | DMSO control | S2-BH3-in | S2-BH3 (400 ug) |
|---|---|---|---|
| Median Survival | 33 days | 35 days | 45 days* |

(n = 12 mice per group,
*p < 0.0001 log rank test)

Example 9

This example illustrates a dose-dependent response to S2-CTMP4 in a human model pancreas adenocarcinoma.

Figure 8:
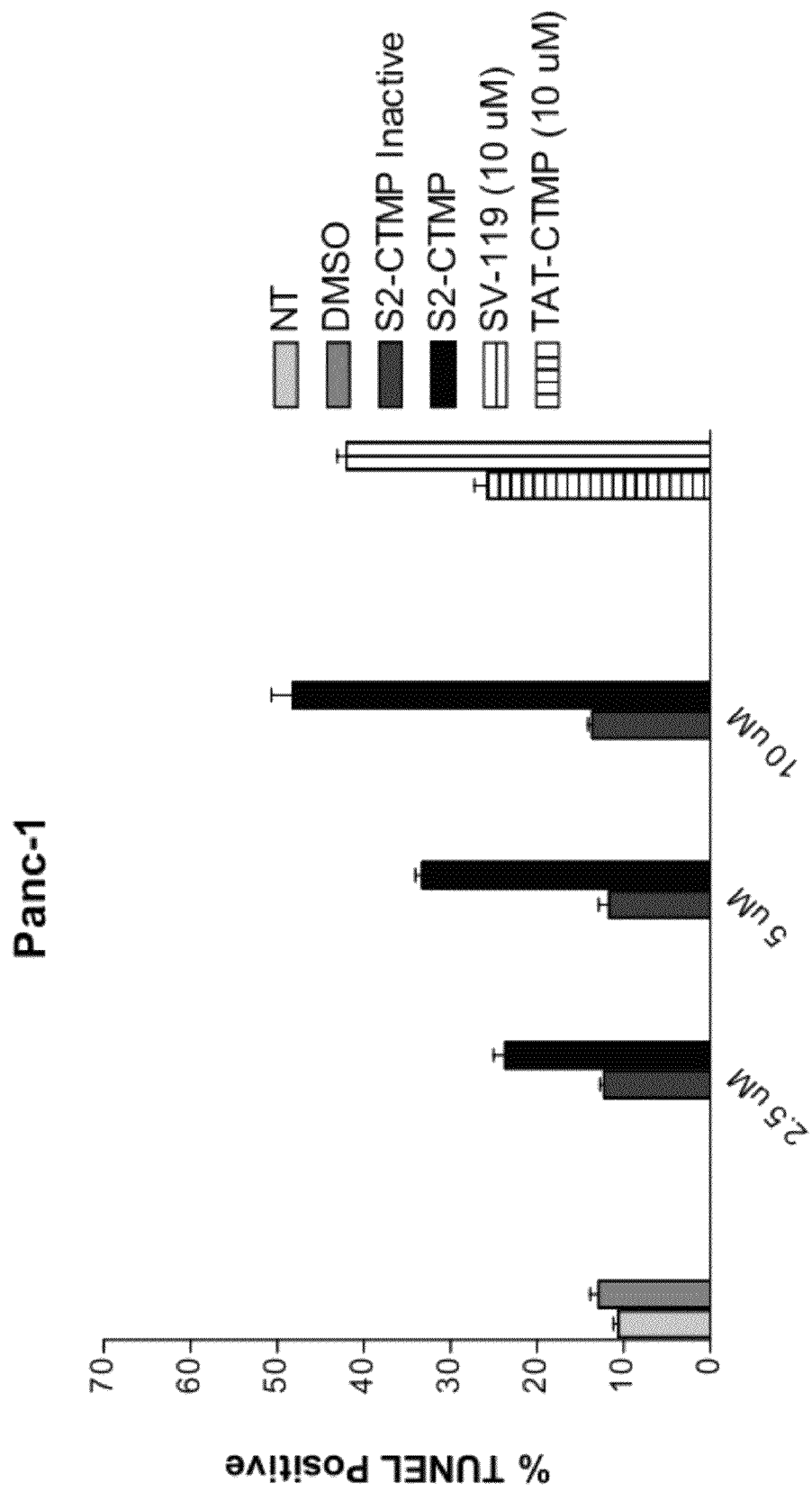
FIG. 8 illustrates a dose-dependent response to S2-CTMP4 in a model human pancreas adenocarcinoma.

In these experiments, human model pancreatic adenocarcinoma (Panc-1) were treated with S2-CTMP4 and S2-CTMP4-Inactive at the outlined concentrations. DMSO (vehicle control), SV119 (S2 Ligand alone), and TAT-CTMP4 were utilized as controls. After 18 hours of treatment, cells were harvested and % active caspase-3 was determined by flow cytometry. Apoptosis was detected using TUNEL (Terminal deoxynucleotidyl Transferase Biotin-dUTP Nick End Labeling). Each experimental group represents an n=3. Results are expressed as the mean, with bars representing standard error of the mean. The results, shown in FIG. 8, indicate strong apoptosis-inducing activity of compound S2-CTMP with respect to Panc-1 human model pancreas adenocarcinoma, both on an absolute scale as well as relative to other compounds.

Example 10

Figure 9:
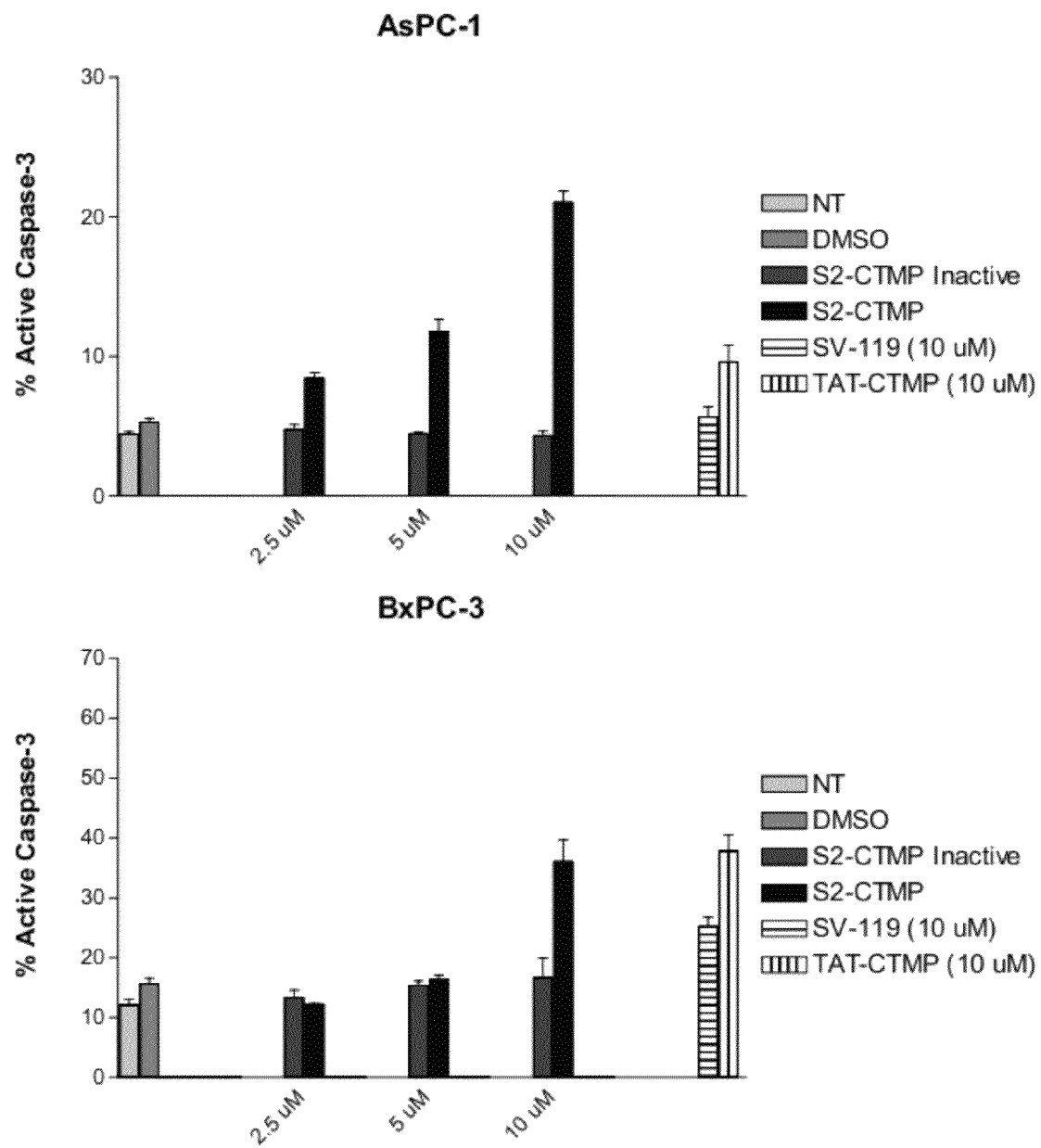
FIG. 9 illustrates a dose-dependent response of S2-CTMP4 in a model human pancreas adenocarcinoma.

This example illustrates a dose-dependent response to S2-CTMP4 in human model pancreas adenocarcinomas. In these experiments, human model pancreatic adenocarcinomas (AsPC-1 and BxPC-3) were treated with S2-CTMP4, S2-CTMP4-Inactive at the outlined concentrations. DMSO (vehicle control), SV119 (S2 Ligand alone), and TAT-CTMP4 were utilized as controls. After 18 hours of treatment, cells were harvested and flow cytometry was used to determine percentage of cells with active caspase-3. Each experimental group represents an n=3. Results are expressed as the mean, with bars representing standard error of the mean. The results, shown in FIG. 9, indicate strong apoptosis-inducing activity of compound S2-CTMP with respect to AsPC-1 and BxPC-3 human model pancreas adenocarcinomas, both on an absolute scale as well as relative to other compounds.

Example 11

This example illustrates that S2-CTMP4 does not induce apoptosis in human donor peripheral blood mononuclear cells (PBMC)

Figure 10:
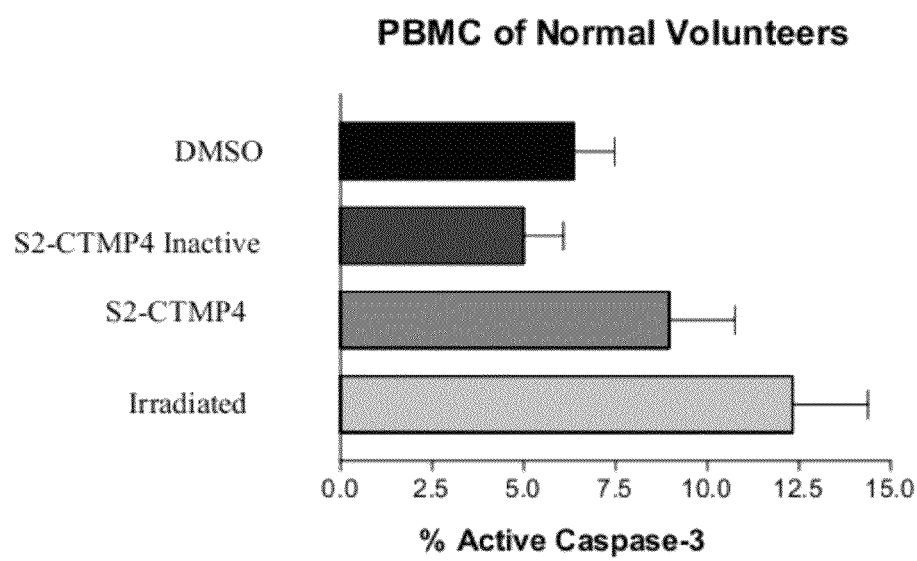
FIG. 10 illustrates that S2-CTMP4 does not induce apoptosis in human donor peripheral blood mononuclear cells (PBMC).

In these experiments, human peripheral blood mononuclear cells were isolated from normal laboratory volunteers. $2.0-3.0 \times 10^6$ PBMC were incubated for 18 h with DMSO (vehicle control), S2-CTMP4-Inactive (10 μM), S2-CTMP4 (10 μM), or after being irradiated at 10,000 rads. % active caspase-3 was subsequently measured by flow cytometry. Each experimental group represents an n=5. Results, displayed in FIG. 10, are expressed as the mean, with bars representing standard error of the mean. The results indicate that S2-CTMP4 causes only a small increase in apoptosis in PBMC, significantly less than the increase in apoptosis resulting from irradiation.

Example 12

This example illustrates that in vivo treatment with S2-BH3 conjugate slows the progression of an allograft pancreatic adenocarcinoma.

Figure 11:
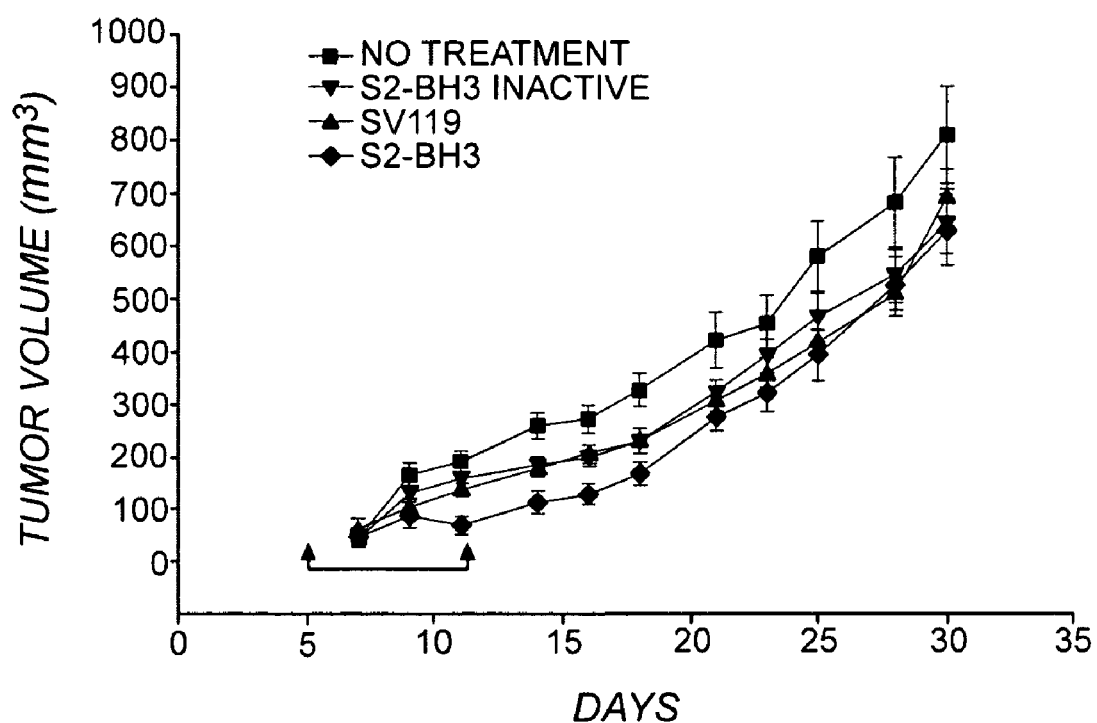
FIG. 11 illustrates that in vivo treatment with S2-BH3 conjugate slows the progression of an allograft pancreatic adenocarcinoma.

In these experiments, n mice received allograft Panc-02 cells, which developed into tumors. During the interval of 5-12 days after receiving the allograft cells, the mice were treated with: S2-BH3-inactive conjugate; sigma-2 ligand SV119; S2-BH3 conjugate; or no treatment (control). Tumor volume was measured at various time intervals. As shown in FIG. 11, the mice receiving S2-BH3 conjugate had measurably smaller tumor volume compared to other treatments, at least until 25 days after receiving the allograft cells.

Example 13

Figure 12:
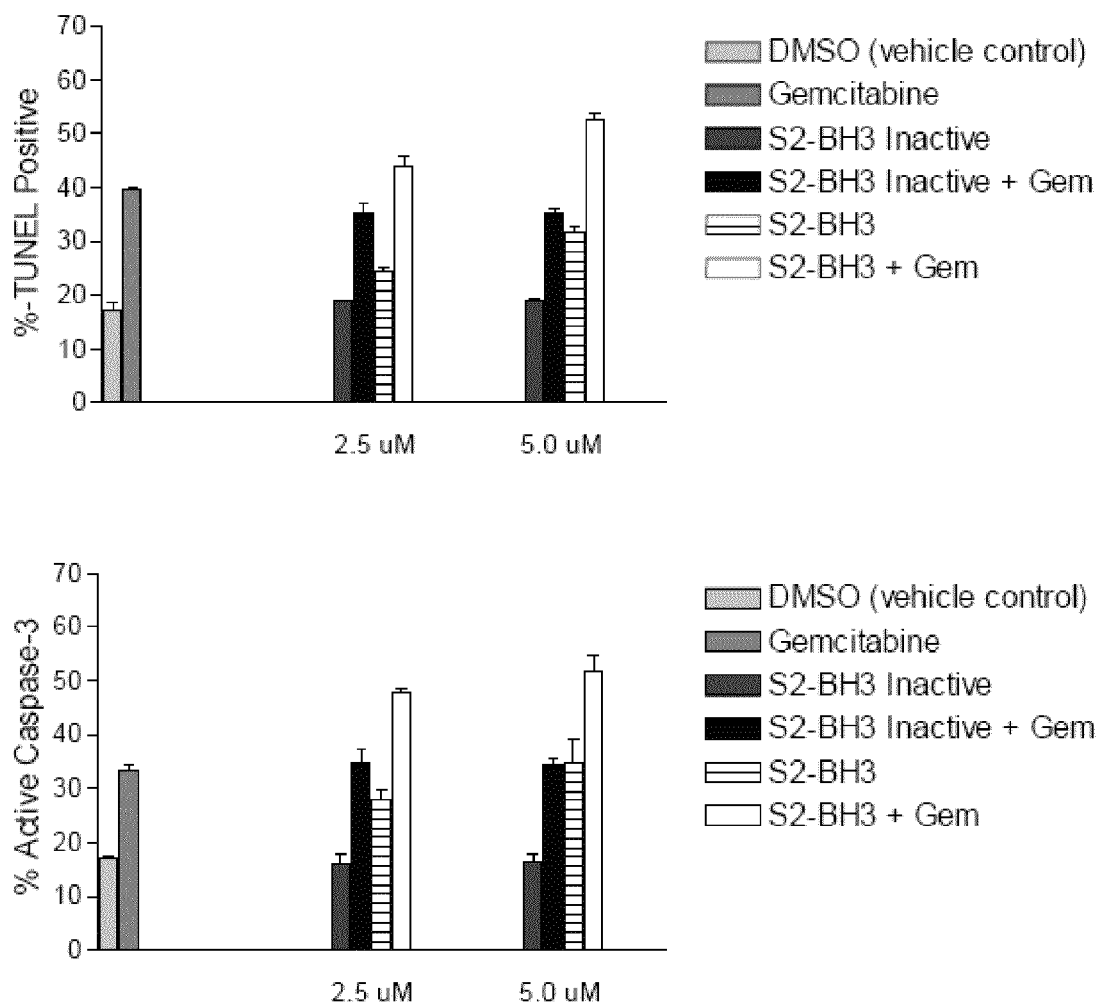
FIG. 12 illustrates that S2-BH3 conjugate has additive cytotoxic activity against a human pancreas adenocarcinoma cell line in vitro when co-administered with a chemotherapeutic agent.

This example illustrates additive cytotoxic activity towards the human pancreas adenocarcinoma cell line Panc1 of S2-BH3 conjugate coadministered with gemcitabine (chemotherapeutic agent of choice for pancreas cancer). In these experiments, human Panc1 adenocarcinoma cells received S2-BH3, S2-BH3-inactive, gemcitabine, S2-BH3+gemcitabine, S2-BH3-inactive+gemcitabine, or DMSO (vehicle control) at 2.5 μM or 5.0 μM. Apoptosis was detected by both active caspase-3 measurement and TUNEL staining on samples harvested at the same time. The results, shown in FIG. 12, indicate an additive effect on apoptosis of co-administration of S2-BH3 and gemcitabine. In this case, the TUNEL staining is the more reliable apoptosis assay due to the transient nature of caspase-3 activation.

Example 14

This example illustrates supra-additive cytotoxic activity towards the human pancreas adenocarcinoma cell line Panc1 of S2-BH3 conjugate coadministered with radiation therapy.

Figure 13:
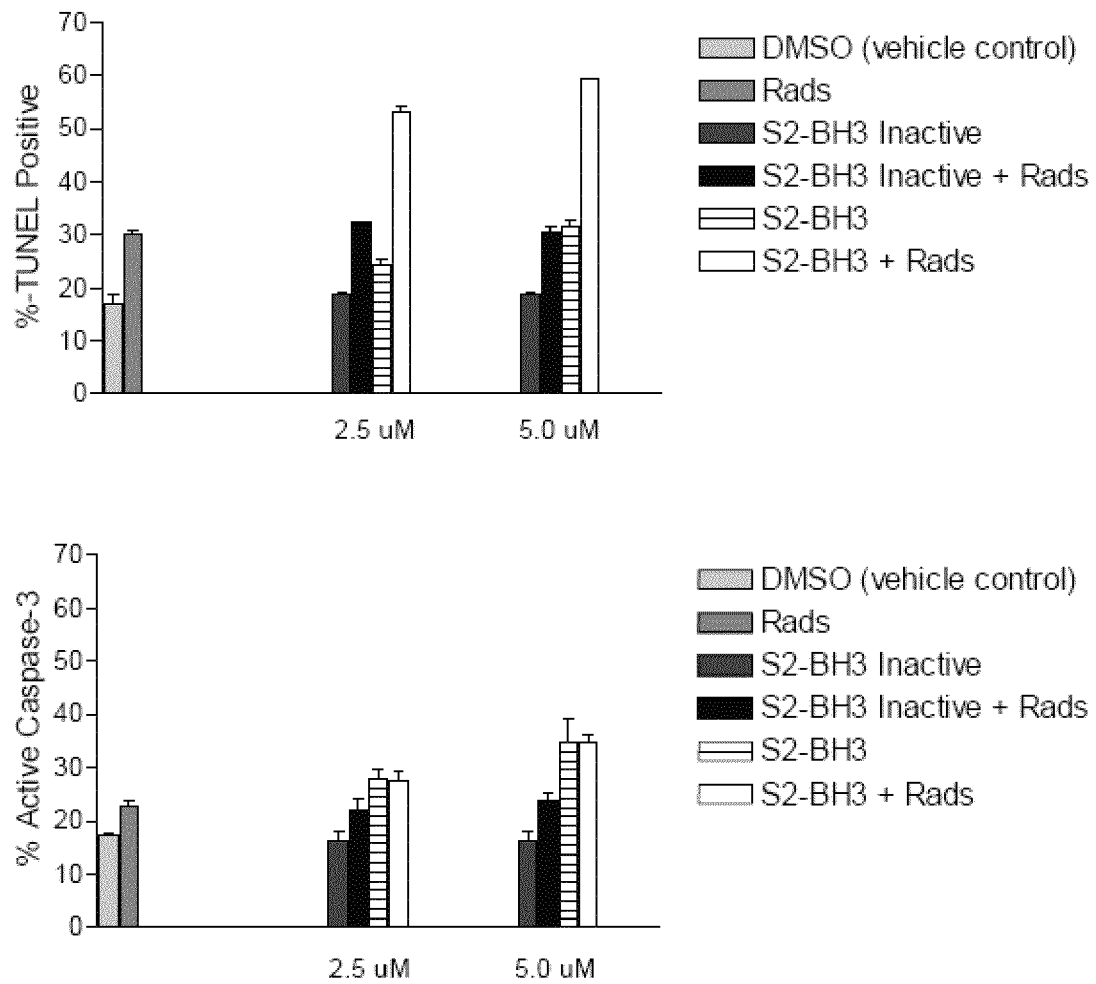
FIG. 13 illustrates that S2-BH3 conjugate has supra-additive cytotoxic activity against a human pancreas adenocarcinoma cell line in vitro when co-administered with radiation therapy.

In these experiments, human Panc1 adenocarcinoma cells received S2-BH3, S2-BH3-inactive, radiation, S2-BH3+radiation, S2-BH3-inactive+radiation, or DMSO (vehicle control) at 2.5 µM or 5.0 µM. Apoptosis was detected by both active caspase-3 measurement and TUNEL staining on samples harvested at the same time. The results, shown in FIG. 13, indicate an additive effect on apoptosis of co-administration of S2-BH3 and gemcitabine. In this case, the TUNEL staining is the more reliable apoptosis assay due to the transient nature of caspase-3 activation.

Example 15

Figure 14:
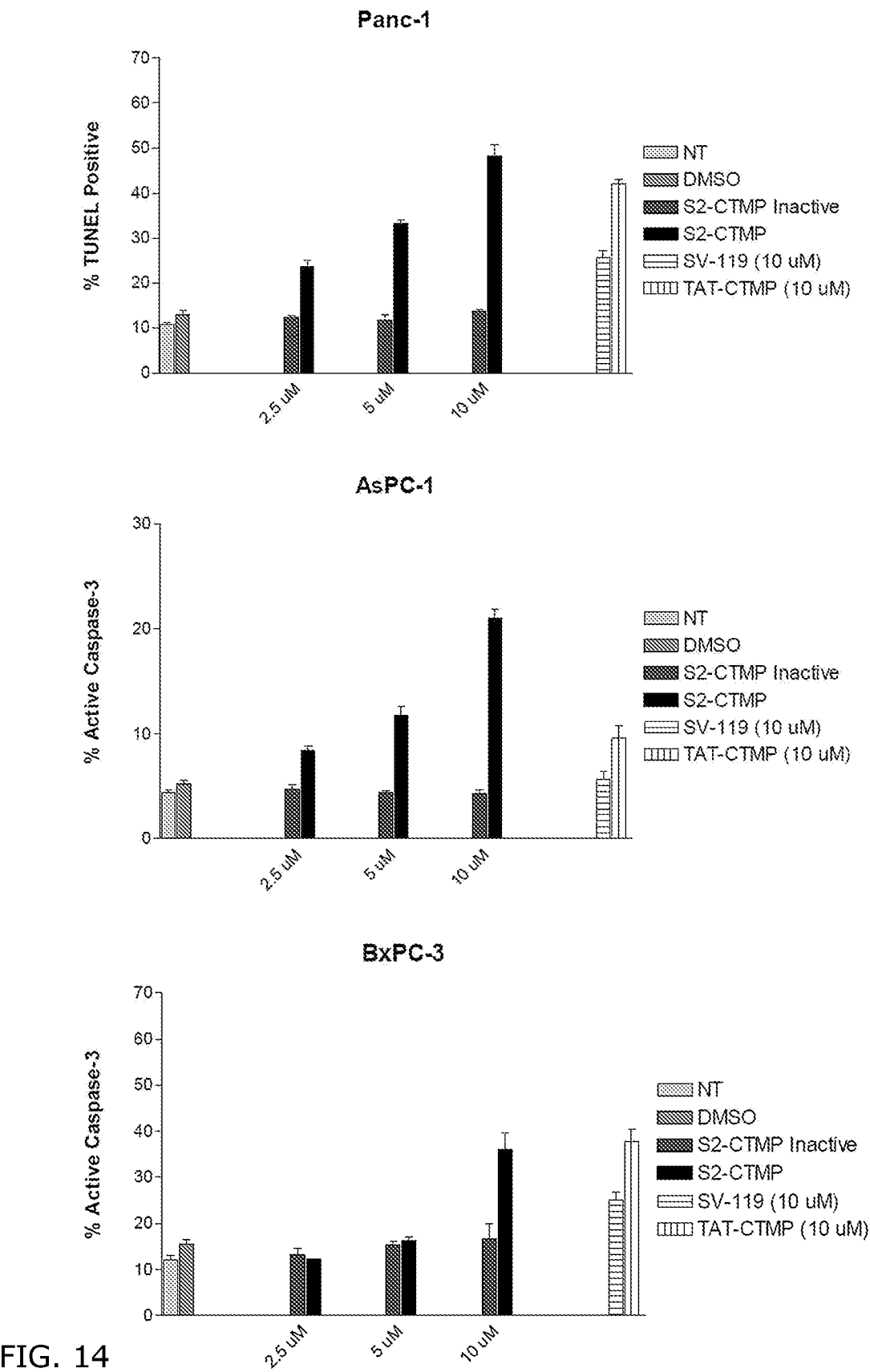
FIG. 14 illustrates cytotoxicity of sigma-2 conjugated CTMP peptide towards a panel of human pancreas adenocarcinoma cell lines in vitro.

This example illustrates the cytotoxicity of the sigma-2 conjugated CTMP peptide towards a panel of human pancreas adenocarcinoma cell lines in vitro. As shown in FIG. 14, Sigma-2 CTMP has equivalent (Panc1, BxPC3) or favorable (AsPC1) cytotoxicity against these cell lines compared to the non-targeted TAT-CTMP peptide.

All publications and patent applications cited in this specification are herein incorporated by reference as if each individual publication or patent application were specifically and individually indicated to be incorporated by reference. Although the foregoing teachings have been described in some detail by way of illustration and example for purposes of clarity of understanding, it will be readily apparent to those of ordinary skill in the art in light of the teachings that certain changes and modifications may be made thereto without departing from the spirit or scope of the appended claims. The present teachings include the following aspects:

1. A compound or a pharmaceutically acceptable salt, prodrug or hydrate thereof, comprising:
   a) a targeting moiety which, in free form, binds a cell receptor with a dissociation constant $K_d$ of less than about $10^{-7}$ M; and
   b) a pharmaceutically active moiety
wherein the targeting moiety is other than an oligopeptide, a polypeptide, a peptidomimetic, a protein or a protein domain, and wherein the targeting moiety and the pharmaceutically active moiety are covalently attached.
2. A compound or a pharmaceutically acceptable salt, prodrug or hydrate thereof in accordance with aspect 1, wherein the targeting moiety in free form binds a cell receptor with a dissociation constant $K_d$ of less than about $10^{-8}$ M.
3. A compound or a pharmaceutically acceptable salt, prodrug or hydrate thereof in accordance with aspect 1, wherein the targeting moiety in free form binds a cell receptor with a dissociation constant $K_d$ of less than about $10^{-9}$ M.
4. A compound or a pharmaceutically acceptable salt, prodrug or hydrate thereof in accordance with aspect 1, wherein the targeting moiety has a molecular mass of less than about 1200 Da.
5. A compound or a pharmaceutically acceptable salt, prodrug or hydrate thereof in accordance with aspect 1, wherein the targeting moiety has a molecular mass of less than about 1000 Da.
6. A compound or a pharmaceutically acceptable salt, prodrug or hydrate thereof in accordance with aspect 1, wherein the targeting moiety has a molecular mass of less than about 800 Da.
7. A compound or a pharmaceutically acceptable salt, prodrug or hydrate thereof in accordance with aspect 1, wherein the targeting moiety has a molecular mass of less than about 400 Da.
8. A compound or a pharmaceutically acceptable salt, prodrug or hydrate thereof in accordance with aspect 1, wherein the cell receptor is a sigma-2 receptor.
9. A compound or a pharmaceutically acceptable salt, prodrug or hydrate thereof in accordance with aspect 8, wherein the targeting moiety binds the sigma-2 receptor with a dissociation constant $K_d$ less than the dissociation constant $K_d$ between the targeting moiety and a sigma-1 receptor.
10. A compound or a pharmaceutically acceptable salt, prodrug or hydrate thereof in accordance with aspect 9, wherein the targeting moiety is a N-substituted 9-azabicyclo[3.3.1]nonan-3α-yl phenylcarbamate.
11. A compound or a pharmaceutically acceptable salt, prodrug or hydrate thereof in accordance with aspect 10, wherein the N-substituted 9-azabicyclo[3.3.1]nonan-3α-yl phenylcarbamate has the structure

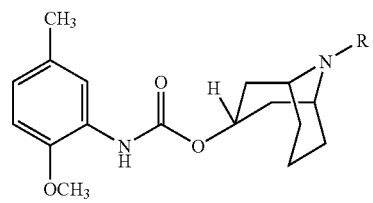

wherein R is selected from the group consisting of a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, an ester and a hydrophilic polymer.
12. A compound or a pharmaceutically acceptable salt, prodrug or hydrate thereof in accordance with aspect 10, wherein the N-substituted 9-azabicyclo[3.3.1]nonan-3α-yl phenylcarbamate has the structure

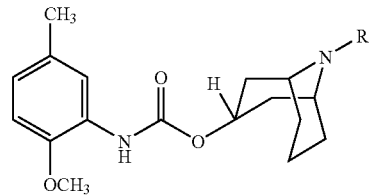

wherein R is a bond.
13. A compound or a pharmaceutically acceptable salt, prodrug or hydrate thereof in accordance with aspect 9, wherein the targeting moiety comprises a dimethoxytetrahydroisoquinoline.
14. A compound or a pharmaceutically acceptable salt, prodrug or hydrate thereof in accordance with aspect 9, wherein the targeting moiety comprises a benzamide and a dimethoxytetrahydroisoquinoline.
15. A compound or a pharmaceutically acceptable salt, prodrug or hydrate thereof in accordance with aspect 1, wherein the cell receptor is a dopamine $D_2$ receptor.
16. A compound or a pharmaceutically acceptable salt, prodrug or hydrate thereof in accordance with aspect 15, wherein the targeting moiety comprises an S-(−) isomer of 3-iodo-2-hydroxy-6-methoxy-N-[(1-ethyl-2-pyrrolidinyl)methyl]benzamide (IBZM).
17. A compound or a pharmaceutically acceptable salt, prodrug or hydrate thereof in accordance with aspect 1, wherein the cell receptor is a dopamine $D_3$ receptor.

18. A compound or a pharmaceutically acceptable salt, prodrug or hydrate thereof in accordance with aspect 17, wherein the targeting moiety comprises 7-hydroxy-N,N-di-n-propyl-2-aminotetralin (7-OH-DPAT).

19. A compound or a pharmaceutically acceptable salt, prodrug or hydrate thereof in accordance with aspect 1, wherein the targeting moiety is selected from the group consisting of colchicine, taxol, cytochalasin, latrunculin, chlorpromazine, spidamine, reserpine, phorbol, a phorbol diester, pioglitazone (Actos™), MK-886, somatostatin receptor agonist, 506BD, methallylrapamycin, rapamycin, and an isatin Michael acceptor.

20. A compound or a pharmaceutically acceptable salt, prodrug or hydrate thereof in accordance with aspect 1, wherein the pharmaceutically active moiety is selected from a peptide and an oligonucleotide.

21. A compound or a pharmaceutically acceptable salt, prodrug or hydrate thereof in accordance with aspect 1, wherein the pharmaceutically active moiety is a bioactive small molecule.

22. A compound or a pharmaceutically acceptable salt, prodrug or hydrate thereof in accordance with aspect 21, wherein the bioactive small molecule is selected from the group consisting of gemcitabine, rapamycin, paclitaxel and 5-fluorouracil.

23. A compound or a pharmaceutically acceptable salt, prodrug or hydrate thereof in accordance with aspect 1, wherein the pharmaceutically active moiety is a cytotoxic moiety.

24. A compound or a pharmaceutically acceptable salt, prodrug or hydrate thereof in accordance with aspect 23, wherein the cytotoxic moiety is an apoptosis-inducing peptide.

25. A compound or a pharmaceutically acceptable salt, prodrug or hydrate thereof in accordance with aspect 24, wherein the apoptosis-inducing peptide comprises an apoptosis-inducing domain of a proapoptotic polypeptide or a variant thereof, wherein the apoptosis-inducing domain of the proapoptotic polypeptide or a variant thereof has apoptosis-inducing activity.

26. A compound or a pharmaceutically acceptable salt, prodrug or hydrate thereof in accordance with aspect 25, wherein the variant of the apoptosis-inducing domain of the proapoptotic polypeptide has at least 50% sequence identity with the apoptosis-inducing domain.

27. A compound or a pharmaceutically acceptable salt, prodrug or hydrate thereof in accordance with aspect 25, wherein the variant of the apoptosis-inducing domain of the proapoptotic polypeptide has at least 95% sequence identity with the apoptosis-inducing domain.

28. A compound or a pharmaceutically acceptable salt, prodrug or hydrate thereof in accordance with aspect 25, wherein the apoptosis-inducing peptide is a Bim polypeptide.

29. A compound or a pharmaceutically acceptable salt, prodrug or hydrate thereof in accordance with aspect 25, wherein the apoptosis-inducing peptide is a BH3 domain of a Bim polypeptide or a variant thereof having apoptosis-inducing activity.

30. A compound or a pharmaceutically acceptable salt, prodrug or hydrate thereof in accordance with aspect 29, wherein the variant of the BH3 domain has at least 50% sequence identity with the BH3 domain of the Bim polypeptide.

31. A compound or a pharmaceutically acceptable salt, prodrug or hydrate thereof in accordance with aspect 29, wherein the variant of the BH3 domain has at least 95% sequence identity with the BH3 domain of the Bim polypeptide.

32. A compound or a pharmaceutically acceptable salt, prodrug or hydrate thereof in accordance with aspect 29, wherein the BH3 domain of the Bim polypeptide comprises the amino acid sequence EIWIAQELRRIGDEFNAYYAR (SEQ ID NO: 1).

33. A compound or a pharmaceutically acceptable salt, prodrug or hydrate thereof in accordance with aspect 29, wherein the BH3 domain of the Bim protein consists of the amino acid sequence EIWIAQELRRIGDEFNAYYAR (SEQ ID NO: 1).

34. A compound or a pharmaceutically acceptable salt, prodrug or hydrate thereof in accordance with aspect 24, wherein the apoptosis-inducing peptide comprises an apoptosis-inducing domain of a negative regulator of an Akt protein kinase, or a variant of the apoptosis-inducing domain, wherein the apoptosis-inducing domain or the variant thereof has apoptosis-inducing activity.

35. A compound or a pharmaceutically acceptable salt, prodrug or hydrate thereof in accordance with aspect 34, wherein the variant has at least 50% sequence identity with the apoptosis-inducing domain.

35. A compound or a pharmaceutically acceptable salt, prodrug or hydrate thereof in accordance with aspect 34, wherein the variant has at least 95% sequence identity with the apoptosis-inducing domain.

36. A compound or a pharmaceutically acceptable salt, prodrug or hydrate thereof in accordance with aspect 34, wherein the apoptosis-inducing domain of a negative regulator of an Akt protein kinase is an apoptosis-inducing domain of a carboxyl terminal modulator protein (CTMP) or a variant thereof, wherein the apoptosis-inducing domain of the CTMP or the variant thereof has apoptosis-inducing activity.

37. A compound or a pharmaceutically acceptable salt, prodrug or hydrate thereof in accordance with aspect 36, wherein the variant of the apoptosis-inducing domain of the CTMP has at least 95% sequence identity with the apoptosis-inducing domain of the CTMP.

38. A compound or a pharmaceutically acceptable salt, prodrug or hydrate thereof in accordance with aspect 36, wherein the apoptosis-inducing domain of the CTMP protein comprises the amino acid sequence LDPKLMKEEQMSQAQLFTRSFDDGL (SEQ ID NO: 2) or a variant thereof having at least 95% sequence identity with SEQ ID NO: 2.

39. A compound or a pharmaceutically acceptable salt, prodrug or hydrate thereof in accordance with aspect 36, wherein the apoptosis-inducing domain of the CTMP protein consists of the amino acid sequence LDPKLMKEEQMSQAQLFTRSFDDGL (SEQ ID NO: 2)

40. A compound or a pharmaceutically acceptable salt, prodrug or hydrate thereof in accordance with aspect 9, wherein the targeting moiety is covalently linked to a peptide having an amino acid sequence selected from the group consisting of EIWIAQELRRIGDEFNAYYAR (SEQ ID NO: 1) and LDPKLMKEEQMSQAQLFTRSFDDGL (SEQ ID NO: 2).

41. A compound or a pharmaceutically acceptable salt, prodrug or hydrate thereof in accordance with aspect 40, wherein the targeting moiety comprises a structure

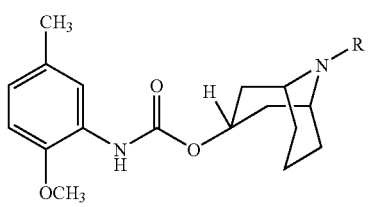

wherein R is selected from the group consisting of a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, an ester, and a hydrophilic polymer.

42. A compound or a pharmaceutically acceptable salt, prodrug or hydrate thereof in accordance with aspect 36, wherein the targeting moiety comprises a structure

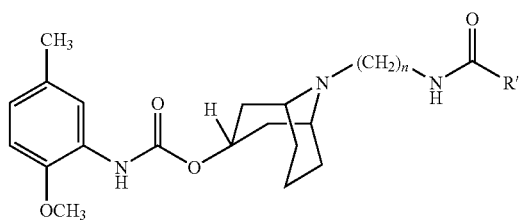

wherein n is an integer from 1 to about 10 and R' is a bond.

43. A compound or a pharmaceutically acceptable salt, prodrug or hydrate thereof in accordance with aspect 42, wherein n=6.
44. A compound or a pharmaceutically acceptable salt, prodrug or hydrate thereof in accordance with aspect 1, wherein the agent selectively induces apoptosis in cells of a target cell population.
45. A compound or a pharmaceutically acceptable salt, prodrug or hydrate thereof in accordance with aspect 44, wherein the cells comprised by a target cell population are cancerous tumor cells.
46. A compound or a pharmaceutically acceptable salt, prodrug or hydrate thereof in accordance with aspect 45, wherein the cancerous tumor cells are pancreatic cancer cells.
47. A pharmaceutical composition comprising the compound of aspect 1 and at least one pharmaceutically acceptable excipient.
48. A pharmaceutical composition comprising the compound of aspect 1 and a pharmaceutically acceptable carrier.
49. A pharmaceutical composition comprising the compound of aspect 1 and at least one additional pharmaceutically active component.
50. A pharmaceutical composition in accordance with aspect 49, wherein the cell receptor is a sigma-2 receptor, the targeting moiety binds the sigma-2 receptor with a dissociation constant $K_d$ less than the dissociation constant $K_d$ between the targeting moiety and a sigma-1 receptor, pharmaceutically active moiety is an apoptosis-inducing peptide, and the at least one additional pharmaceutically active component is a chemotherapeutic agent.
51. A pharmaceutical composition in accordance with aspect 50, wherein the chemotherapeutic agent is gemcitabine.
52. A method of treating a cancer, comprising administering to a subject in need of treatment of a cancer an effective amount of the compound of aspect 9.
53. A method of treating a cancer in accordance with aspect 52, wherein the targeting moiety is an N-substituted 9-azabicyclo[3.3.1]nonan-3α-yl phenylcarbamate of structure

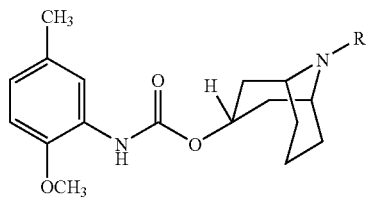

wherein R is a bond.

54. A method of treating a cancer in accordance with aspect 52, wherein the pharmaceutically active moiety is selected from a peptide and an oligonucleotide.
55. A method of treating a cancer in accordance with aspect 52, wherein the pharmaceutically active moiety is a peptide having apoptosis-inducing activity.
56. A method of treating a cancer in accordance with aspect 52, wherein the oligopeptide having apoptosis-inducing activity is selected from the group consisting of a BH3 domain of a Bim polypeptide, a variant thereof, an apoptosis-inducing domain of a negative regulator of an Akt protein kinase and a variant thereof.
57. A method of treating a cancer in accordance with aspect 52, wherein the targeting moiety is covalently linked to a peptide having an amino acid sequence selected from the group consisting of EIWIAQELRRIGDEFNAYYAR (SEQ ID NO: 1) and LDPKLMKEEQMSQAQLFTRS-FDDGL (SEQ ID NO: 2).
58. A method of treating a cancer in accordance with aspect 52, wherein the cancer is a pancreatic cancer.
59. A method of treating a cancer in accordance with aspect 52, further comprising administering an effective amount of a chemotherapeutic agent to the subject.
60. A method of treating a cancer in accordance with aspect 59, wherein the chemotherapeutic agent is gemcitabine.
61. A method of treating a cancer in accordance with aspect 52, further comprising administering radiation therapy to the subject.
62. A method of treating a cancer, comprising:
    selecting a pharmaceutical composition on the basis of the composition comprising a pharmaceutical compound comprising a non-peptide targeting moiety which selectively targets a proapoptotic moiety to a sigma-2 receptor of tumor cells; and
    administering an effective amount of the composition to a subject in need of treatment for a cancer.
63. A method of treating a cancer in accordance with aspect 62, wherein the compound selectively targets a proapoptotic moiety to mitochondria of tumor cells.
64. A method of treating a cancer in accordance with aspect 62, wherein the proapoptotic moiety comprises a proapoptotic peptide.
65. A method of treating a cancer in accordance with aspect 64, wherein the targeting moiety comprises

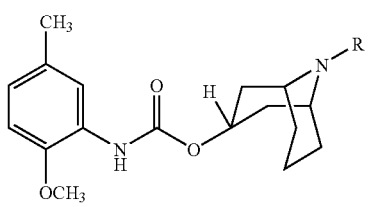

wherein R is a bond.

66. A method of treating a cancer in accordance with aspect 64, wherein the pharmaceutically active moiety is a peptide having apoptosis-inducing activity, and comprises a sequence selected from the group consisting of EIWIAQELRRIGDEFNAYYAR (SEQ ID NO: 1), a variant thereof having at least 90% sequence similarity. LDPKLMKEEOMSOAOLFTRSFDDGL (SEQ ID NO: 2) and a variant thereof having at least 90% sequence similarity.

67. Use of a therapeutic agent for the manufacture of a medicament for treatment of a cancer, wherein the therapeutic agent comprises a) a targeting moiety which, in free form, binds a cell receptor with a dissociation constant $K_d$ of less than about $10^{-7}$ M, and b) a pharmaceutically active moiety, wherein the targeting moiety is other than an oligopeptide, a polypeptide, a peptidomimetic a protein or a protein domain, and wherein the targeting moiety and the pharmaceutically active moiety are covalently attached.

68. Use of a therapeutic agent in accordance with aspect 67, wherein the cell receptor is a sigma-2 receptor.

69. Use of a therapeutic agent in accordance with aspect 68, wherein the targeting moiety comprises

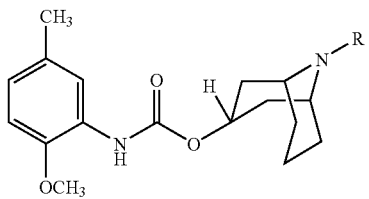

wherein R is a bond.

70. Use of a therapeutic agent in accordance with aspect 69, wherein the pharmaceutically active moiety is a peptide having apoptosis-inducing activity, and comprises a sequence selected from the group consisting of EIWIAQELRRIGDEFNAYYAR (SEQ ID NO: 1), a variant thereof having at least 90% sequence similarity LDPKLMKEEQMSQAQLFTRSFDDGL (SEQ ID NO: 2) and a variant thereof having at least 90% sequence similarity.

71. A method of inducing apoptosis in a cell, comprising: contacting the cell with a compound comprising a) a non-peptide targeting moiety which, in free form, has a molecular weight of less than about 1200 Da and binds a sigma-2 receptor with a dissociation constant $K_d$ of less than about $10^{-7}$ M, and b) a proapoptotic peptide moiety.

72. A method of inducing apoptosis in accordance with aspect 71, wherein the targeting moiety comprises

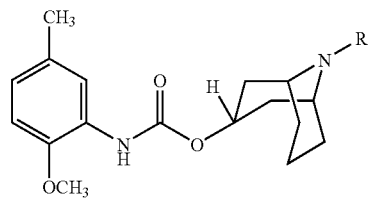

wherein R is a bond.

73. A method of inducing apoptosis in accordance with aspect 71, wherein the proapoptotic peptide moiety comprises a sequence selected from the group consisting of EIWIAQELRRIGDEFNAYYAR (SEQ ID NO: 1), a variant thereof having at least 90% sequence similarity, LDPKLMKEEQMSQAQLFTRSFDDGL (SEQ ID NO: 2) and a variant thereof having at least 90% sequence similarity, and wherein the peptide or variant thereof has proapoptotic activity.

74. A method of inducing apoptosis in accordance with aspect 73, wherein the variant of the peptide having sequence EIWIAQELRRIGDEFNAYYAR (SEQ ID NO: 1) has at least 95% sequence similarity and wherein the variant of the peptide having sequence LDPKLMKEEQMSQAQLFTRSFDDGL (SEQ ID NO: 2) has at least 95% sequence similarity, and wherein the peptide or variant thereof has proapoptotic activity.

What is claimed is:

1. A compound or a pharmaceutically acceptable salt, prodrug or hydrate thereof, comprising:
    a) a targeting moiety which, in free form, binds a cell receptor with a dissociation constant Kd of less than about $10^{-7}$ M; and
    b) a pharmaceutically active moiety wherein the targeting moiety is other than an oligopeptide, a polypeptide, a peptidominietic, a protein or a protein domain, and wherein the targeting moiety and the pharmaceutically active moiety are covalently attached, and, wherein the pharmaceutically active moiety is an apoptosis-inducing peptide.

2. A compound or a pharmaceutically acceptable salt, prodrug or hydrate thereof in accordance with claim 1, wherein the apoptosis-inducing peptide comprises an apoptosis-inducing domain of a proapoptotic polypeptide or a variant thereof, wherein the apoptosis-inducing domain of the proapoptotic polypeptide or a variant thereof has apoptosis-inducing activity, and wherein the variant of the apoptosis-inducing domain of the proapoptotic polypeptide has at least 50% sequence identity with the apoptosis-inducing domain.

3. A compound or a pharmaceutically acceptable salt, prodrug or hydrate thereof in accordance with claim 2, wherein the apoptosis-inducing peptide is a Bim polypeptide, a BH3 domain of a Bim polypeptide or a variant thereof having apoptosis-inducing activity and having at least 95% sequence identity with the BH3 domain of the Bim polypeptide.

4. A compound or a pharmaceutically acceptable salt, prodrug or hydrate thereof comprising:
    a) a targeting moiety which, in free form, binds a cell receptor with a dissociation constant Kd of less than about $10^{-7}$ M; and
    b) a pharmaceutically active moiety wherein the targeting moiety is other than an oligopeptide, a polypeptide, a peptidomimetic, a protein or a protein domain, and wherein the targeting moiety and the pharmaceutically active moiety are covalently attached, wherein the cell receptor is a sigma-2 receptor, and wherein the targeting moiety is covalently linked to a peptide having an amino acid sequence selected from the group consisting of EIWIAQELRRRIGDEFNAYYAR (SEQ ID NO: 1) and LDPKLMKEEQMSQAQLFTRSFDDGL (SEQ ID NO: 2).

5. A compound or a pharmaceutically acceptable salt, prodrug or hydrate thereof in accordance with claim 4, wherein the targeting moiety comprises a structure

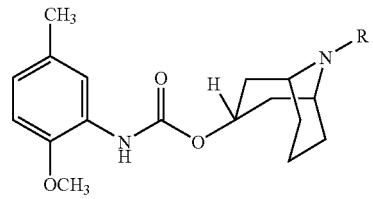

wherein R is selected from the group consisting of a bond, a $C_1$-$C_{10}$ alkyl, a $C_1$-$C_{10}$ alkylamine, a $C_1$-$C_{10}$ alkylamide, a $C_1$-$C_{10}$ heteroalkyl, a $C_1$-$C_{10}$ aryl, a $C_1$-$C_{10}$ heteroaryl, an ester, and a hydrophilic polymer.

6. A method of treating a cancer, comprising administering to a subject in need of treatment of a cancer an effective amount of a compound or a pharmaceutically acceptable salt, prodrug or hydrate thereof, comprising:
    a) a targeting moiety which, in free form, binds a cell receptor with a dissociation constant Kd of less than about $10^{-7}$ M and is an N-substituted 9-azabicyclo [3.3.1]nonan-3α-yl phenylcarbamate of structure

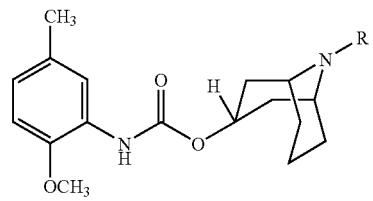

wherein R is a bond, and
    b) a pharmaceutically active moiety
wherein the targeting moiety and the pharmaceutically active moiety are covalently attached, and wherein the pharmaceutically active moiety is a peptide having apoptosis-inducing activity and is selected from the group consisting of a BH3 domain of a Bim polypeptide, a variant thereof having apoptosis-inducing activity, an apoptosis-inducing domain of a negative regulator of an Akt protein kinase and a variant thereof having apoptosis-inducing activity.

7. A method of treating a cancer in accordance with claim 6, wherein the cancer is a pancreatic cancer.

8. A method of inducing apoptosis in a cell, comprising:
contacting the cell with a compound comprising a) a non-peptide targeting moiety which, in free form, has a molecular weight of less than about 1200 Da and binds a sigma-2 receptor with a dissociation constant Kd of less than about $10^{-7}$ M, and b) a proapoptotic peptide moiety.

9. A method of inducing apoptosis in accordance with claim 8, wherein the targeting moiety comprises

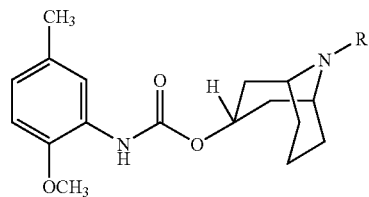

wherein R is a bond.

10. A method of inducing apoptosis in accordance with claim 8, wherein the proapoptotic peptide moiety comprises a sequence selected from the group consisting of EIWIAQEL-RRIGDEFNAYYAR (SEQ ID NO: 1), a variant thereof having at least 90% sequence similarity, LDPKLMKEEQM-SQAQLFTRSFDDGL (SEQ ID NO: 2) and a variant thereof having at least 90% sequence similarity, and wherein the peptide or variant thereof has proapoptotic activity.

* * * * *